US007666429B2

(12) United States Patent
Thomas et al.

(10) Patent No.: US 7,666,429 B2
(45) Date of Patent: *Feb. 23, 2010

(54) **NUCLEIC ACIDS ENCODING A HOUSE DUST MITE ALLERGEN *DER P* III, AND USES THEREFOR**

(75) Inventors: Wayne R. Thomas, Nedlands (AU); Kaw-Yan Chua, Taipei (TW); Bruce L. Rogers, Belmont, MA (US); Mei-Chang Kuo, Winchester, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/846,341

(22) Filed: May 14, 2004

(65) Prior Publication Data

US 2005/0123569 A1    Jun. 9, 2005

Related U.S. Application Data

(60) Continuation of application No. 08/462,515, filed on Jun. 5, 1995, now Pat. No. 6,752,991, which is a division of application No. 08/163,919, filed on Dec. 8, 1993, now Pat. No. 6,180,771.

(51) Int. Cl.
*A01N 37/18* (2006.01)
*A61K 38/00* (2006.01)
*A61K 39/00* (2006.01)
*A61K 39/35* (2006.01)
*A61K 39/36* (2006.01)
*C07K 2/00* (2006.01)
*C07K 4/00* (2006.01)
*C07K 5/00* (2006.01)
*C07K 7/00* (2006.01)
*C07K 14/00* (2006.01)
*C07K 16/00* (2006.01)
*C07K 17/00* (2006.01)

(52) U.S. Cl. .................. 424/185.1; 424/275.1; 514/2; 530/300; 530/326

(58) Field of Classification Search ............... None
See application file for complete search history.

(56) References Cited

U.S. PATENT DOCUMENTS

| 5,314,991 | A | | 5/1994 | Oka et al. |
| 5,338,663 | A | * | 8/1994 | Potter et al. ................ 435/4 |
| 5,506,097 | A | * | 4/1996 | Potter et al. ................ 435/4 |
| 5,710,126 | A | * | 1/1998 | Griffith et al. .............. 514/12 |
| 6,180,771 | B1 | | 1/2001 | Thomas et al. |
| 6,752,991 | B1 | | 6/2004 | Thomas et al. |
| 2004/0092446 | A1 | * | 5/2004 | Goulmy et al. ............. 514/12 |

FOREIGN PATENT DOCUMENTS

WO            93/08279 A1    4/1993

OTHER PUBLICATIONS

Goldsby et al., Immunology, 5th edition W.H. Freeman and Company, 2003, pp. 62-698.*
Colman, PM, Research in Immunology, 1994, 145:33-36.*
Burks et al., Eur J Biochem, 1997, 245:334-339.*
Janeway et al., Immunobiology, 3rd edition, Garland Press, 1997, pp. 4:24-4:30.*
Blumenthal et al., in Allergen and allergen Immunotherapy, 3rd edition, 2004, Marcel Decker Inc, pp. 37-49.*
Malandain, H. 'Basic Immunology, allergen prediction, and bioinformatics.' Allergy. 59:1011-1012, 2004.*
Salomon et al. 'Predicting Class II MHC-Peptide binding: a kernel based approach using similarity scores.' BMC Bioinfomatics 7:501-512, 2006.*
Goldsby et at., Immunology, 5th edition, 2003, W.H.Freeman and Company, pp. 62-67.*
King et al. J. Immunol. 166:6057-6065, 2001.*
Blumenthal et al., in Allergens and Allergen Immunotherapy, 2004, Marcel Dekker, Inc., pp. 37-50.*
Burks et al., Eur. J. Biochem, 1997, 245:334-339.*
IUPAC-IUB. 'Nomenclature and Symbolism for Amino Acids and Peptides.' Biochem. J. 219:345-373, 1984.*
Baldo et al. (1989) "Toward a Definition of the 'Complete' Spectrum and Rank Order of Importance of the Allergens from the House Dust Mite: *Dermatophagoides pteronyssinus*" *Adv. BioScience 74*: 13-31.
Bengtsson et al. (1986) "Detection of Allergens in Mould and Mite Preparations by a Nitrocellulose Electroblotting Technique" *Int. Arch. Appl. Immun. 80*: 383-390.
Boswell and Lesk (1988) "Sequence Comparison and Alignment: the Measurement and Interpretation of Sequence Similarity" in *Computational Molecular Biology*, A.M. Lesk, Ed. (New York: Oxford University Press) Chp. 14: 161-178.
Chua et al. (1988)"Sequence Analysis of cDNA Coding for a Major House Dust Mite Allergen, *Der p 1*" *J. Exp. Med. 167*: 175-182.
Chua, K.Y., et al., "Isolation of cDNA Coding for the Major Mite Allergen *Der p* II by IgE Plaque Immunoassay," *Int Arch Allergy Appl Immunol*, vol. 91:118-123 (1990).
Editors of *The Lancet* (1989) "Corrections" *The Lancet 2*: 462.
Fletcher et al. (1987) "Isolation and Characterization of a cDNA Encoding Rat Cationic Trypsinogen" *Biochemistry 26*: 3081-3086.
Lind (1985) "Purification and Partial Characterization of Two Major Allergens From the House Dust Mite *Dermatophagoides pteronyssinus*" *Journal of Allergy and Clinical Immunology 76*(5): 753-761.
Lind et al. (1983) "Identification of Allergens in *Dermatophagoides pteronyssinus* Mite Body Extract by Crossed Radioimmunoelectrophoresis with Two Different Rabbit Antibody Pools" *Scand. J. Immunol. 17*: 263-273.

(Continued)

*Primary Examiner*—Maher M Haddad
*Assistant Examiner*—Nora M Rooney
(74) *Attorney, Agent, or Firm*—Arent Fox LLP

(57) ABSTRACT

Isolated nucleic acids encoding an allergen of *Dermatophagoides pteronyssinus*, Der p III, are disclosed. A cDNA encoding a peptide having a Der p III activity and a predicted molecular weight of about 24,985 daltons is also described. The nucleic acids can be used as probes to detect the presence of Der p III nucleic acid in a sample or for the recombinant production of peptides having an activity of Der p III. Peptides having an activity of Der p III can be used in compositions suitable for pharmaceutical administration or methods of diagnosing sensitivity to house dust mites.

10 Claims, 3 Drawing Sheets

OTHER PUBLICATIONS

O'Hehir et al. (1989) "Clonal Analysis of the Cellular Immune Response to the House Dust Mite *Dermatophagoides farinae*" *Int Arch. Allergy Appl. Immunol.* 88: 170-172.

Shen et al. (1993) "Molecular Cloning of a House Dust Mite Allergen With Common Antibody Binding Specificities with Multiple Components in Mite Extracts" *Clinical and Experimental Allergy* 23: 934-940.

Smith, et al., "Cloning and sequencing of the *Dermatophagoides pteronyssinus* group III allergen, Der p III," *Clinical and Experimental Allergy*, vol. 24:220-228 (1994).

Stewart et al. (1992) "The Group III Allergen from the House Dust Mite *Dermatophagoides pteronyssinus* is a Trypsin-like Enzym" *Immunology* 75: 29-35.

Stewart et al. (1987) "In Vitro Translation of Messenger RNA from House Dust Mite *Dermatophagoides pteronyssinus*" *Int. Archs. Allergy Appl. Immunol.* 83: 384-389.

Stewart et al. (1989) "Protease Antigens from the House Dust Mite" *Lancet 2*: 154-155.

Stewart, Geoffrey A., et al., "A comparative study of allergenic and potentially allergenic enzymes and *Dermatophagoides pteronyssinus, D. farinae and Euroglyphus maynei*," *Experimental & Applied Acarology*, vol. 16:165-180 (1992).

Tovey et al. (1987) "Comparison by Electroblotting of IgE-binding Components in Extracts of House Dust Mite Bodies and Spent Mite Culture" *Journal of Allergy and Clinical Immunology* 79(1): 93-102.

Yasueda et al. (1993) "Allergens From *Dermatophagoides* Mites With Chymotryptic Activity" *Clinical and Experimental Allergy* 23(5): 384-390.

\* cited by examiner

```
                                                                          CT     2
TTTTTTTTTTTTTTTGAAAACATTGAAAAACATTGAAGCAACTGTGTGTACAACCAGAAAG            62
ATGATCATCTATAATATTTTAATTGTTTTATTATTGGCCATTAATACATTGGCTAATCCA           122
 M  I  I  Y  N  I  L  I  V  L  L  A  I  N  T  L  A  N  P
-29                         -20                            -10

ATTCTACCAGCATCACCAAATGCAACTATTGTTGGTGGTGAAAAAGCATTAGCTGGTGAA           182
 I  L  P  A  S  P  N  A  T  I  V  G  G  E  K  A  L  A  G  E
                           1                          10

TGTCCATATCAGATTTCATTACAATCAAGTAGTCATTTTTGTGGTGGTACTATTCTTGAT           242
 C  P  Y  Q  I  S  L  Q  S  S  S  H  F  C  G  G  T  I  L  D
                 20                           30

GAATATTGGATTTTAACAGCTGCACATTGTGTTGCCGGACAAACAGCAAGTAAACTTTCA           302
 E  Y  W  I  L  T  A  A  H  C  V  A  G  Q  T  A  S  K  L  S
                       40                         50

ATTCGTTACAATAGTTTAAAACATTCATTAGGTGGTGAAAAAATTTCTGTTGCTAAAATT           362
 I  R  Y  N  S  L  K  H  S  L  G  G  E  K  I  S  V  A  K  I
                       60                         70

TTTGCACATGAAAAATATGATAGTTATCAAATTGATAATGATATTGCATTGATTAAGCTT          422
 F  A  H  E  K  Y  D  S  Y  Q  I  D  N  D  I  A  L  I  K  L
                    80                           90

AAATCACCTATGAAATTAAATCAGAAAAATGCCAAAGCTGTTGGATTACCAGCAAAAGGA           482
 K  S  P  M  K  L  N  Q  K  N  A  K  A  V  G  L  P  A  K  G
                   100                          110

TCGGATGTAAAAGTTGGTGATCAAGTTCGTGTTTCTGGTTGGGGTTATCTTGAAGAAGGA           542
 S  D  V  K  V  G  D  Q  V  R  V  S  G  W  G  Y  L  E  E  G
                     120                         130

AGTTATTCATTACCATCTGAATTAAGACGTGTTGATATTGCTGTTGTATCACGTAAAGAA           602
 S  Y  S  L  P  S  E  L  R  R  V  D  I  A  V  V  S  R  K  E
                    140                         150

TGTAATGAATTATATTCAAAAGCTAATGCTGAAGTTACTGATAATATGATTTGTGGTGGT           662
 C  N  E  L  Y  S  K  A  N  A  E  V  T  D  N  M  I  C  G  G
                    160                         170

GATGTTGCAAATGGTGGTAAAGATTCTTGTCAAGGTGATTCTGGTGGACCGGTTGTTGAT           722
 D  V  A  N  G  G  K  D  S  C  Q  G  D  S  G  G  P  V  V  D
                    180                         190

GTTAAAAATAATCAAGTTGTTGGTATTGTTTCATGGGGTTATGGTTGTGCACGTAAAGGT           782
 V  K  N  N  Q  V  V  G  I  V  S  W  G  Y  G  C  A  R  K  G
                    200                         210

TATCCAGGTGTTTATACACGTGTTGGTAATTTTATCGATTGGATTGAATCAAAACGTTCA           842
 Y  P  G  V  Y  T  R  V  G  N  F  I  D  W  I  E  S  K  R  S
                    220                         230

CAGTGATTGATAAAAACAATTTCGACATATAAAAATTGGCAAATGATGCCATTATATGTT           902
 Q  *
ATCATTATGTTTCTGGTGATTCTTTTTCTACTTTTATCATTTTATTTTATATTCGAGCTG           962
AAAACAAACAATCATGATTGTATAGGGATTTGTTGTTGTTTTCAATTTAAAAAAATCCA          1022
AAATAAATAAATAAATAATCATTTCAACAAAAAAAG                                 1059
```

Fig. 1

```
DerpIII    MIIYNILIVL LLAINTLANP ILPASPNATI VGGEKALAGE CPYQISLQS-   49
CRAYFISH   ---------- ---------- ---------I VGGTDAVLGE FPYQLSFQET   21

Consensus  .......... .......... .........I VGG..A..GE .PYQ.S.Q..   50

DerpIII    ----SSHFCG GTILDEYWIL TAAHCVAG-- -QTASKLSIR YNSLKHSL--    90
CRAYFISH   FLGFSFHFCG ASIYNENYAI TAGHCVYGDD YENPSGLQIV AGELDMSVNE    71

Consensus  ....S.HFCG ...I..E.... TA.HCV.G.. ....S.L.I. ...L..S...   100

DerpIII    GGEK-ISVAK IFAHEKYDSY QIDNDIALIK LKSPMKLNQK NAKAVGLPAK   139
CRAYFISH   GSEQTITVSK IILHENFDYD LLDNDISLLK LSGSLTFN-N NVAPIALPAQ   120

Consensus  G.E..I.V.K I..HE..D.. ..DNDI.L.K L......N.. N.....LPA.   150

DerpIII    GSDVKVGDQV RVSGWGYLEE GSYSLPSELR RVDIAVVSRK ECNELYSKAN   189
CRAYFISH   G-HTATGN-V IVTGWGTTSE GG-NTPDVLQ KVTVPLVSDA ECRDDY--GA   165

Consensus  G.....G..V .V.GWG...E G....P..L. .V....VS.. EC...Y....   200

DerpIII    AEVTDNMICG GDVANGGKDS CQGDSGGPVV --DVKNNQVV GIVSWGYGCA   237
CRAYFISH   DEIFDSMICA G-VPEGGKDS CQGDSGGPLA ASDTGSTYLA GIVSWGYGCA   214

Consensus  .E..D.MIC. G.V..GGKDS CQGDSGGP.. ...D....... GIVSWGYGCA   250

DerpIII    RKGYPGVYTR VGNFIDWIES KRSQ                              261
CRAYFISH   RPGYPGVYTE VSYHVDWIKA N-AV                              237

Consensus  R.GYPGVYT. V....DWI.. ....                              274
```

NUCLEIC ACIDS ENCODING A HOUSE DUST MITE ALLERGEN DER P III, AND USES THEREFOR

BACKGROUND OF THE INVENTION

Approximately 10% of the population become hypersensitized (allergic) upon exposure to antigens from a variety of environmental sources. Those antigens that induce immediate and/or delayed types of hypersensitivity are known as allergens (King, T. P., (1976) *Adv. Immunol.*, 23:77-105). Allergens can include products of grasses, trees, weeds, animal dander, insects, food, drugs, and chemicals. Genetic predisposition of an individual is believed to play a role in the development of immediate allergic responses (Young, R. P. et al., (1990) *Clin. Sci.*, 79:19) such as atopy and anaphylaxis, whose symptoms include hay fever, asthma, and hives.

The antibodies involved in atopic allergy belong primarily to the IgE class of immunoglobulins. IgE binds to basophils, mast cells and dendritic cells via a specific, high-affinity receptor FcɛRI (Kinet, J. P., (1990) *Curr. Opin. Immunol.*, 2:499-505). Upon combination of an allergen acting as a ligand with its cognate receptor IgE, FcɛRI bound to the IgE may be cross-linked on the cell surface, resulting in physiological manifestations of the IgE—allergen interaction. These physiological effects include the release of, among other substances, histamine, serotonin, heparin, chemotactic factor(s) for eosinophilic leukocytes and/or leukotrienes C4, D4, and E4, which cause prolonged constriction of bronchial smooth muscle cells (Hood, L. E. et al., *Immunology* (2nd ed.), The Benjamin/Cumming Publishing Co., Inc. (1984)). Hence, the ultimate consequence of the interaction of an allergen with IgE is allergic symptoms triggered by the release of the aforementioned mediators. Such symptoms may be systemic or local in nature, depending on the route of entry of the antigen and the pattern of deposition of IgE on mast cells or basophils. Local manifestations generally occur on epithelial surfaces at the site of entry of the allergen. Systemic effects can induce anaphylaxis (anaphylactic shock) which results from IgE-basophil response to circulating (intravascular) antigen.

Studies with purified allergens have shown that about 80% of patients allergic to the mite *Dermatophagoides pteronyssinus* produce IgE reactive to Der p I and Der p II (Chapman M. D. et al., *J. Immunol.* (1980) 125:587-92; Lind P., *J. Allergy Clin. Immunol.* (1985) 76:753-61; Van der Zee J. S. et al, *J. Allergy Clin. Immunol.* (1988) 81:884-95). For about half the patients these specificities constitute 50% of the IgE antimite antibody. The allergen Der p III, recently identified as trypsin, (Stewart G. A. et al., *Immunology* (1992) 75:29-35) reacts with a similar or higher frequency (Stewart G. A. et al, supra; Ford S. A. et al., *Clin. Exp. Allergy* (1989) 20:27-31). However, in the only quantitative study reported to date, the investigators determined that the level of IgE binding to Der p III was considerably less than for Der p I. Electrophoretic techniques (Ford S. A. et al., supra; Bengtsson A. et al., *Int. Arch. Allergy Appl. Immunol.* (1986) 80:383-90; Lind P. et al., *Scand. J. Immunol.* (1983) 17:263-73; Tovey E. R. et al., *J. Allergy Clin. Immunol.* (1987) 79:93-102) have shown that most sera contain IgE which recognize other allergens.

The significance of the IgE reactivity to Der p III remains uncertain. The reactivity of this group of allergens has been reported to be as low as 16% using a fluid phase assay (Heymann et al., *J Allergy Clin Immunol* (1989) 83: 1055-1067) and as high as 100% using RAST assay (Stewart et al., *Immunology* (1992) 75: 29-35). Several others have reported IgE reactivity between 60-83% (Tovey et al., *J Allergy Clin Immunol* (1987) 22: 93-102; Thomas et al., *Exp Appl Acarol* (1992) 16: 153-164; Yasueda et al., *Clin Exp Allergy* (1993) 23:384-390). The discrepancies in the frequency of IgE reactivity to the group III allergens may be attributable to either the differences in the purity of the allergen preparation studied or the differences in sensitivity of the assay techniques used. In order to determine the importance of particular specificities in the allergic reactions, there is a need for quantities of pure allergen, which would enable quantitative IgE binding tests and studies of the frequency and lymphokine profile of T cell responses to the allergen.

Many patients with sensitivity to house dust mite allergens are treated currently by administration of small, gradually increasing doses of house dust mite extracts. Use of these extracts has multiple drawbacks, including potential anaphylaxis during treatment and the necessity of continuing therapy, often for a period of several years to build up sufficient tolerance and significant diminution of clinical symptoms. The ability to substitute compositions of house dust mite allergen, Der p III, would overcome several of these drawbacks. Thus, a source of pure allergen that could be provided in quantity for use as a diagnostic or therapeutic reagent and therapeutic methods that would overcome the drawbacks associated with house dust mite extracts are highly desirable.

SUMMARY OF INVENTION

This invention provides isolated nucleic acids encoding peptides having at least one biological activity of Der p III, an allergen of the species *Dermatophagoides pteronyssinus* (house dust mite). A preferred nucleic acid is a cDNA having a nucleotide sequence shown in FIG. 1 (SEQ ID NO:1). The invention also pertains to peptides encoded by all or a portion of such cDNA (SEQ ID NO: 1) and having at least one biological activity of Der p III. Also contemplated are isolated nucleic acids which hybridize under high stringency conditions (e.g., equivalent to 20-27° C. below $T_m$ and 1M NaCl) to a nucleic acid having a nucleotide sequence shown in FIG. 1 (SEQ ID NO: 1) or which encodes a peptide comprising all or a portion of an amino acid sequence of FIG. 1 (SEQ ID NO:2). Nucleic acids which encode peptides having an activity of Der p III and having at least 50% homology with a sequence shown in FIG. 1 (SEQ ID NO:2) are also featured. Peptides having a Der p III activity produced by recombinant expression of a nucleic acid of the invention, and peptides having a Der p III activity prepared by chemical synthesis are also featured by this invention. Preferred peptides have the ability to induce a T cell response which can include T cell stimulation (measured by, for example, T cell proliferation or cytokine secretion) or T cell non-responsiveness (i.e., contact with the peptide or a complex of the peptide with an MHC molecule of an antigen presenting cell induces the T cell to become unresponsive to stimulatory signals or incapable of proliferation). Other preferred peptides either apart from or in addition to the ability to induce a T cell response, have the ability to bind specific IgE of house dust mite-allergic subjects. Such peptides are useful in diagnosing sensitivity to house dust mites in a subject. Still other peptides, either apart from or in addition to the ability to induce a T cell response, have a significantly reduced or negligible ability to bind house dust mite-allergic IgE. Such peptides are particularly useful as therapeutic agents.

Other preferred peptides comprise an amino acid sequence shown in FIG. 1 (SEQ ID NO:2). In one embodiment, peptides having a Der p III activity and comprising a portion of the amino acid sequence of FIG. 1 (SEQ ID NO:2) are at least about 8-30 amino acids in length, preferably about 10-20 amino acids in length, and most preferably about 10-16 amino acids in length.

Another aspect of the invention features antibodies specifically reactive with peptides having a Der p III activity. Peptides having an activity of Der p III can be used in compositions suitable for pharmaceutical administration. For example, such compositions can be used in a manner similar to house dust mite extracts to treat or prevent allergic reactions to house dust mites in a subject. Nucleic acids of the invention and peptides having an activity of Der p III can also be used for diagnosing sensitivity in a subject to house dust mites.

BRIEF DESCRIPTION OF THE DRAWINGS

FIG. 1 shows the complete nucleotide (SEQ ID NO:1) and deduced amino acid (SEQ ID NO:2) sequences of the Der p III clone.

FIG. 2 shows the amino acid sequences of Der p III (SEQ ID NO:2) and a trypsin protein from crayfish (SEQ ID NO:3).

DETAILED DESCRIPTION OF THE INVENTION

Figure 3:
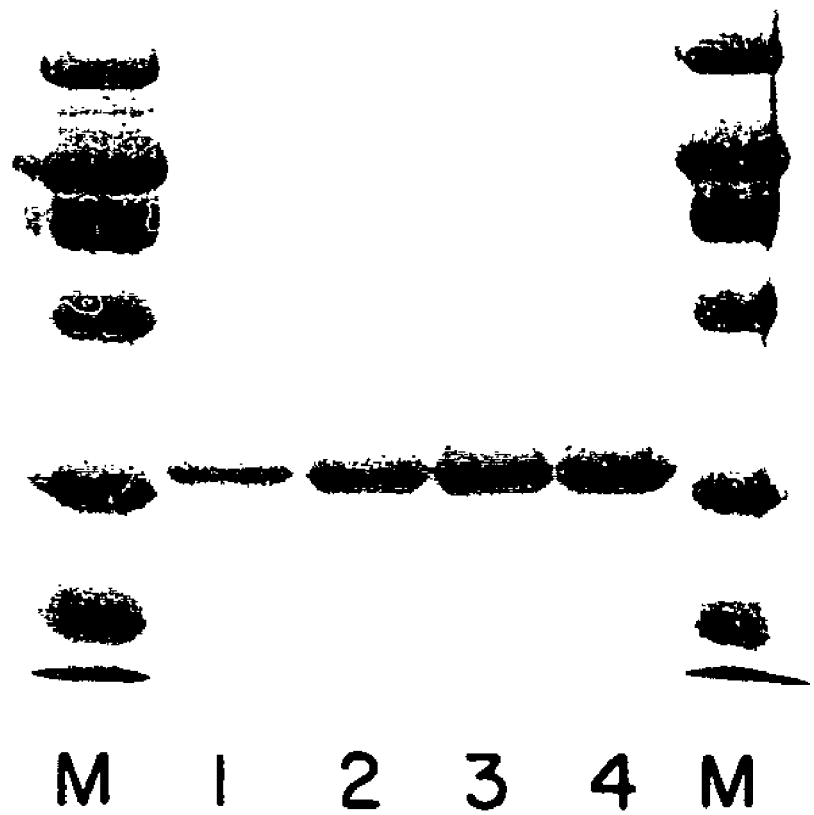
FIG. 3 shows the results of SDS-PAGE analysis of various concentrations of recombinant Der p III (lane 1, 4.3 µg; lane 2, 8.7 µg; lane 3, 13.8 µg; lane 4, 17.4 µg; markers are indicated by M).

This invention pertains to isolated nucleic acids encoding peptides having at least one biological activity of Der p III, a Group III allergen of the species *Dermatophagoides pteronyssinus*. Preferably, the nucleic acid is a cDNA comprising a nucleotide sequence shown in FIG. 1 (SEQ ID NO:1).

The cDNA shown in FIG. 1 (SEQ ID NO: 1) encodes a Der p III peptide which includes a predicted 29 amino acid residue pre-pro region encoded by nucleotides 63 through 149. This leader sequence is not found in the mature Der p III which is encoded by nucleotides 150 through 845. The deduced amino acid sequence based on this cDNA is also shown in FIG. 1 (SEQ ID NO:2). The cDNA encodes a 232 residue mature peptide having a predicted molecular weight of 24,985 daltons including seven cysteine residues. A polyadenylation signal sequence 179 nucleotides after the last base is present in the cDNA (See FIG. 1). A culture of *E. coli* transfected with an expression vector containing the cDNA encoding Der p III was deposited under the Budapest Treaty with the American Type Culture Collection on Oct. 15, 1993 and assigned accession number 69472.

Accordingly, one aspect of this invention pertains to isolated nucleic acids comprising a nucleotide sequence encoding Der p III, fragments thereof encoding peptides having at least one biological activity of Der p III and/or equivalents of such nucleic acids. The term nucleic acid as used herein is intended to include such fragments and equivalents. The term equivalent is intended to include nucleotide sequences encoding functionally equivalent Der p III peptides having an activity of Der p III. As defined herein, a peptide having an activity of Der p III has at least one biological activity of the Der p III allergen. Equivalent nucleotide sequences include sequences that differ by one or more nucleotide substitutions, additions or deletions, such as allelic variants, and include sequences that differ from the nucleotide sequence encoding Der p III shown in FIG. 1 (SEQ ID NO: 1) due to the degeneracy of the genetic code. Equivalents includes nucleotide sequences that hybridize under stringent conditions (i.e., equivalent to about 20-27° C. below melting temperature ($T_m$) and about 1M NaCl) to the nucleotide sequence of Der p III shown in FIG. 1 (SEQ ID NO:1).

Peptides referred to herein as having an activity of Der p III or having a Der p III activity are defined herein as peptides that have an amino acid sequence corresponding to all or a portion of the amino acid sequence of Der p III shown in FIG. 1 (SEQ ID NO:2). For example, a peptide having an activity of Der p III may have the ability to induce a response in Der p III restricted T cells such as stimulation (e.g., T cell proliferation or cytokine secretion) or induce T cell non-responsiveness. Alternatively, or additionally, a peptide having an activity of Der p III may have the ability to bind (to be recognized by) immunoglobulin E antibodies of house dust mite-allergic subjects. Peptides which bind IgE are useful in methods of detecting allergic sensitivity to Der p III in a subject. Peptides that do not bind IgE, or bind IgE to a lesser extent than a purified, native Der p III protein binds IgE are particularly useful as therapeutic agents.

In one embodiment, the nucleic acid is a cDNA encoding a peptide having an activity of Der p III. Preferably, the nucleic acid is a cDNA molecule comprising at least a portion of the nucleotide sequence encoding Der p III shown in FIG. 1 (SEQ ID NO: 1). A preferred portion of the cDNA molecule of FIG. 1 (SEQ ID NO: 1) includes the coding region of the molecule.

In another embodiment, the nucleic acid of the invention encodes a peptide having an activity of Der p III and comprising an amino acid sequence shown in FIG. 1 (SEQ ID NO:2). Preferred nucleic acids encode a peptide having a Der p III activity and having at least about 50% homology, more preferably at least about 60% homology and most preferably at least about 70% homology with the sequence shown in FIG. 1 (SEQ ID NO:2). Nucleic acids which encode peptides having a Der p III activity and having at least about 90%, more preferably at least about 95%, and most preferably at least about 98-99% homology with a sequence set forth in FIG. 1 (SEQ ID NO:2) are also within the scope of the invention. Homology refers to sequence similarity between two peptides having an activity of Der p III or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

Another aspect of the invention provides a nucleic acid that hybridizes under high or low stringency conditions to a nucleic acid encoding a peptide having all or a portion of an amino acid sequence shown in FIG. 1 (SEQ ID NO:2). Appropriate stringency conditions which promote DNA hybridization, for example, 6.0× sodium chloride/sodium citrate (SSC) at about 45° C., followed by a wash of 2.0×SSC at 50° are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids encoding a peptide having an activity of Der p III, as described herein, and having a sequence that differs from the nucleotide sequence shown in FIG. 1 (SEQ ID NO: 1) due to degeneracy in the genetic code are also within the scope of the invention. Such nucleic acids differ in sequence from the sequence of FIG. 1 (SEQ ID NO: 1) encode functionally equivalent peptides (i.e., peptides having an activity of Der p III), but due to degeneracy in the genetic code. For example, a number of amino acids are designated by more than one triplet. Codons that specify the same amino acid, or synonyms (for example, CAU and CAC are synonyms for histidine) may result in "silent" mutations that do not affect the amino acid sequence of the Der p III protein. However, it is expected that DNA sequence polymorphisms that do lead to changes in the amino acid sequence of Der p III will exist within the house dust mite population. One skilled in the art will appreciate that these variations in one or more nucleotides (up to about 3-4% of the nucleotides) of the nucleic acids encoding peptides having an activity of Der p III may exist among individual house dust mites due to natural allelic variation. Any and all such nucleotide variations and resulting amino acid polymorphisms are within the scope of this invention. Furthermore, there may be one or more isoforms or related, cross-reacting family members of Der p III. Such isoforms or family members are defined as proteins related in function and amino acid sequence to Der p III, but are encoded by genes at different loci.

Fragments of a nucleic acid encoding Der p III are also within the scope of the invention. As used herein, a fragment of a nucleic acid encoding Der p III refers to a nucleotide sequence having fewer nucleotides than the nucleotide sequence encoding the entire amino acid sequence of Der p III protein and which encodes a peptide having an activity of Der p III (i.e., a peptide having at least one biological activity of the Der p III allergen) as defined herein.

Preferred nucleic acid fragments encode peptides of at least 10 amino acid residues in length, preferably about 10-20 amino acid residues in length, and more preferably about 10-16 amino acid residues in length. Nucleic acid fragments that encode peptides having a Der p III activity of at least about 30 amino acid residues in length, at least about 40 amino acid residues in length, at least about 60 amino acid residues in length, at least about 80 amino acid residues in length, at least about 100 amino acid residues in length, and at least about 200 amino acid residues in length or more are also within the scope of this invention.

Nucleic acid fragments within the scope of the invention include those capable of hybridizing under high or low stringency with nucleic acids from other animal species for use in screening protocols to detect Der p III or allergens that are cross-reactive with Der p III. Generally, the nucleic acid encoding a peptide having an activity of Der p III will be selected from the bases encoding the mature protein, however, in some instances, it may be desirable to select all or part of a peptide from the leader sequence portion of the nucleic acid of the invention. Nucleic acids within the scope of the invention may also contain linker sequences, modified restriction endonuclease sites and other sequences useful for molecular cloning, expression or purification of recombinant peptides having an activity of Der p III.

A nucleic acid encoding a peptide having an activity of Der p III may be obtained from mRNA present in house dust mites of the species *Dermatophagoides pteronyssinus*. It should also be possible to obtain nucleic acids encoding Der p III from *Dermatophagoides pteronyssinus* genomic DNA. For example, the gene encoding Der p III can be cloned from either a cDNA or a genomic library in accordance with protocols herein described. A cDNA encoding Der p III can be obtained by isolating total mRNA from *Dermatophagoides pteronyssinus*. Double stranded cDNAs can then be prepared from the total mRNA. Subsequently, the cDNAs can be inserted into a suitable plasmid or bacteriophage vector using any one of a number of known techniques. Genes encoding Der p III can also be cloned using established polymerase chain reaction techniques in accordance with the nucleotide sequence information provided by the invention. The nucleic acids of the invention can be DNA or RNA. A preferred nucleic acid is a cDNA encoding Der p III having the sequence depicted in FIG. 1 (SEQ ID NO: 1).

This invention also provides expression vectors containing a nucleic acid encoding a peptide having an activity of Der p III operably linked to at least one regulatory sequence. Operably linked is intended to mean that the nucleotide sequence is linked to a regulatory sequence in a manner which allows expression of the nucleotide sequence. Regulatory sequences are art-recognized and are selected to direct expression of the peptide having an activity of Der p III by a transfected host cell. Accordingly, the term regulatory sequence includes promoters, enhancers and other expression control elements. Such regulatory sequences are described in Goeddel, *Gene Expression Technology: Methods in Enzymology* 185, Academic Press, San Diego, Calif. (1990). It should be understood that the design of the expression vector may depend on such factors as the choice of the host cell to be transformed and/or the type of protein desired to be expressed. In one embodiment, the expression vector includes a DNA encoding a peptide having an activity of Der p III. Such expression vectors can be used to transfect cells to thereby produce proteins or peptides, including fusion proteins or peptides encoded by nucleic acids as described herein.

This invention further pertains to a host cell transfected to express a peptide having an activity of Der p III. The host cell may be any procaryotic or eucaryotic cell. For example, a peptide having an activity of Der p III may be expressed in bacterial cells such as *E. coli*, insect cells (baculovirus), yeast, or mammalian cells such as Chinese hamster ovary cell (CHO). Other suitable host cells are referred to in Goeddel (1990), supra, or known to those skilled in the art.

Expression in eucaryotic cells such as mammalian, yeast, or insect cells can lead to partial or complete glycosylation and/or formation of relevant inter- or intra-chain disulfide bonds of a recombinant peptide product. Examples of vectors for expression in yeast *S. cerivisae* include pYepSec1 (Baldari. et al., (1987) *Embo J.* 6:229-234), pMFa (Kurjan and Herskowitz, (1982) *Cell* 30:933-943), pJRY88 (Schultz et al, (1987) *Gene* 54:113-123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 2:2156-2165) and the pVL series (Lucklow, V. A., and Summers, M. D., (1989) *Virology* 170:31-39). Generally, COS cells (Gluzman, Y., (1981) *Cell* 2:175-182) are used in conjunction with such vectors as pCDM 8 (Aruffo, A. and Seed, B., (1987) *Proc. Natl. Acad. Sci. USA* 84:8573-8577) for transient amplification/expression in mammalian cells, while CHO (dhfr⁻ Chinese Hamster Ovary) cells are used with vectors such as pMT2PC (Kaufman et al., (1987), *EMBO J.* 6:187-195) for stable amplification/expression in mammalian cells. Vector DNA can be introduced into mammalian cells via conventional techniques such as calcium phosphate or calcium chloride co-precipitation, DEAE-dextran-mediated transfection, or electroporation. Suitable methods for transforming host cells can be found in Sambrook et al. (*Molecular Cloning: A Laboratory Manual,* 2nd Edition, Cold Spring Harbor Laboratory press (1989)), and other laboratory textbooks.

Expression in procaryotes is most often carried out in *E. coli* with either fusion or non-fusion inducible expression vectors. Fusion vectors usually add a number of NH$_2$ terminal amino acids to the expressed target gene. These NH$_2$ terminal amino acids often are referred to as a reporter group. Such reporter groups usually serve two purposes: 1) to increase the solubility of the target recombinant protein; and 2) to aid in the purification of the target recombinant protein by acting as a ligand in affinity purification. Often, in fusion expression vectors, a proteolytic cleavage site is introduced at the junction of the reporter group and the target recombinant protein to enable separation of the target recombinant protein from the reporter group subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein. A preferred reporter group is poly(His), which renders the recombinant fusion protein easily purifiable by metal chelate chromatography.

Inducible non-fusion expression vectors include pTrc (Amann et al., (1988) *Gene* 69:301-315) and pET11d (Studier et al., *Gene Expression Technology: Methods in Enzymology* 185, Academic Press, San Diego, Calif. (1990) 60-89). While target gene expression relies on host RNA polymerase transcription from the hybrid trp-lac fusion promoter in pTrc, expression of target genes inserted into pET11d relies on transcription from the T7 gn10-lac 0 fusion promoter mediated by coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

One strategy to maximize recombinant Der p III expression in *E. coli* is to express the protein in a host bacteria with an impaired capacity to proteolytically cleave the recombinant protein (Gottesman, S., *Gene Expression Technology: Methods in Enzmology* 185, Academic Press, San Diego, Calif. (1990) 119-128). Another strategy would be to alter the nucleic acid encoding Der p III to be inserted into an expression vector so that the individual codons for each amino acid would be those preferentially utilized in highly expressed *E. coli* proteins (Wada et al, (1992) *Nuc. Acids Res.* 20:2111-2118). Such alteration of nucleic acids of the invention can be carried out by standard DNA synthesis techniques.

The nucleic acids of the invention can also be chemically synthesized using standard techniques. Various methods of chemically synthesizing polydeoxynucleotides are known, including solid-phase synthesis which, like peptide synthesis, has been fully automated in commercially available DNA synthesizers (See, e.g., Itakura et al., U.S. Pat. No. 4,598,049; Caruthers et al., U.S. Pat. No. 4,458,066; and Itakura U.S. Pat. Nos. 4,401,796 and 4,373,071, incorporated by reference herein).

The present invention further pertains to methods of producing peptides that have an activity of Der p III. For example, a host cell transfected with a nucleic acid vector directing expression of a nucleotide sequence encoding a peptide having an activity of Der p III can be cultured under appropriate conditions to allow expression of the peptide to occur. The peptide may be secreted and isolated from a mixture of cells and medium containing the peptide. Alternatively, the peptide may be retained cytoplasmically and the cells harvested, lysed and the protein isolated. A cell culture includes host cells, media and other byproducts. Suitable media for cell culture are well known in the art. Peptides of the invention can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptides.

Another aspect of the invention pertains to isolated peptides having an activity of Der p III. A peptide having an activity of Der p III has at least one biological activity of the Der p III allergen. For example, a peptide having an activity of Der p III may have the ability to induce a response in Der p III specific T cells such as stimulation (T cell proliferation or cytokine secretion) or induce T cell non-responsiveness. In one embodiment, a peptide having an activity of Der p III stimulates T cells as evidenced by, for example, T cell proliferation or cytokine secretion. In another embodiment, peptides having a Der p III activity induce T cell non-responsiveness in which T cells are unresponsive to a subsequent challenge with a Der p III peptide or native Der p III protein following exposure to the peptide. In yet another embodiment, a peptide having a Der p III activity has reduced IgE binding activity compared to purified, native Der p III protein. A peptide having an activity of Der p III may differ in amino acid sequence from the Der p III sequence depicted in FIG. 1 (SEQ ID NO:2) but such differences result in a modified protein which functions in the same or similar manner as a native Der p III protein or which has the same or similar characteristics of Der p III protein. Various modifications of the Der p III protein to produce these and other functionally equivalent peptides are described in detail herein. The term peptide, as used herein, refers to peptides, proteins, and polypeptides.

A peptide can be produced by modification of the amino acid sequence of the Der p III protein shown in FIG. 1 (SEQ ID NO:2), such as by a substitution, addition, or deletion of one or more amino acid residues. Such modifications may be directed to amino acid residues not involved in a biological activity of the peptide, or the modifications may be directed to such amino acid residues in order to enhance, or eliminate a particular biological activity. Peptides of the invention are at least about 8 amino acid residues in length, preferably about 10-20 amino acid residues in length and more preferably about 10-16 amino acid residues in length. Peptides having an activity of Der p III of at least about 30 amino acid residues in length, at least about 40 amino acid residues in length, at least about 60 amino acid residues in length, at least about 80 amino acid residues in length, at least about 100 amino acid residues in length, and at least about 200 amino acid residues or more in length are also included within the scope of this invention.

In another embodiment of the invention, peptides from a related Group III allergen of the species *Dermatophagoides farinae*, Der f III, are provided. Such peptides have been isolated from a purified, native Der f III protein and comprise the sequences: IVGGVKAKAGDSPYQISLQSSSH-FXGGSILD (SEQ ID NO: 15), an N-terminal sequence; MICGGDVANGGVDSEQGD (SEQ ID NO: 10), an internal peptide; and MTLDQTNAKPVPLPTS (SEQ ID NO:12), an internal peptide.

Yet another embodiment of the invention provides a substantially pure preparation of a peptide having an activity of Der p III. Such a preparation is substantially free of proteins and peptides with which the peptide naturally occurs (i.e., other house dust mite peptides), either in a cell or when secreted by a cell.

The term isolated as used herein refers to a nucleic acid or peptide that is substantially free of cellular material or culture medium when produced by recombinant DNA techniques, or chemical precursors or other chemicals when chemically synthesized. Such peptides are also characterized as being free of all other house dust mite proteins. Accordingly, an isolated peptide having an activity of Der p III is produced recombinantly or synthetically and is substantially free of cellular material and culture medium or substantially free of chemical precursors or other chemicals and is free of all other house dust mite proteins. An isolated nucleic acid is also free of sequences which naturally flank the nucleic acid (i.e., sequences located at the 5' and 3' ends of the nucleic acid) in the organism from which the nucleic acid is derived.

Peptides having an activity of Der p III can be obtained, for example, by screening peptides recombinantly produced from the corresponding fragment of the nucleic acid of Der p III encoding such peptides. In addition, fragments can be chemically synthesized using techniques known in the art such as conventional Merrifield solid phase f-Moc or t-Boc chemistry. For example, the Der p III protein may be arbitrarily divided into fragments of desired length with no overlap of the fragments, or preferably divided into overlapping fragments of a desired length. The fragments can be produced (recombinantly or by chemical synthesis) and tested to identify those peptides having a Der p III activity, i.e., the ability to induce a T cell response such as T cell stimulation (T cell proliferation, cytokine secretion) or T cell non-responsiveness, and/or has reduced IgE binding activity.

In one embodiment, peptides having an activity of Der p III can be identified by the ability of the peptide to stimulate T cells or to induce T cell non-responsiveness. Peptides which stimulate T cells, as determined by, for example, T cell proliferation or cytokine secretion are defined herein as comprising at least one T cell epitope. T cell epitopes are believed to be involved in initiation and perpetuation of the immune response to the protein allergen which is responsible for the clinical symptoms of allergy. These T cell epitopes are thought to trigger early events at the level of the T helper cell by binding to an appropriate HLA molecule on the surface of an antigen presenting cell, thereby stimulating the T cell subpopulation with the relevant T cell receptor for the epitope. These events lead to T cell proliferation, lymphokine secretion, local inflammatory reactions, recruitment of additional immune cells to the site of antigen/T cell interaction, and activation of the B cell cascade, leading to the production of antibodies. One isotype of these antibodies, IgE, is fundamentally important to the development of allergic symptoms and its production is influenced early in the cascade of events at the level of the T helper cell, by the nature of the lymphokines secreted. A T cell epitope is the basic element, or smallest unit of recognition by a T cell receptor, where the epitope comprises amino acids essential to receptor recognition. Amino acid sequences which mimic those of the T cell epitopes and which modify the allergic response to protein allergens are within the scope of this invention.

Screening peptides for those which retain a Der p III activity as described herein can be accomplished using one or more of several different assays. For example, in vitro, Der p III T cell stimulatory activity is assayed by contacting a peptide known or suspected of having a Der p III activity with an antigen presenting cell which presents appropriate MHC molecules in a T cell culture. Presentation of a peptide having a Der p III activity in association with appropriate MHC molecules to T cells in conjunction with the necessary costimulation has the effect of transmitting a signal to the T cell that induces the production of increased levels of cytokines, particularly of interleukin-2 and interleukin-4. The culture supernatant can be obtained and assayed for interleukin-2 or other known cytokines. For example, any one of several conventional assays for interleukin-2 can be employed, such as the assay described in *Proc. Natl. Acad. Sci USA*, 86:1333 (1989), the pertinent portions of which are incorporated herein by reference. A kit for an assay for the production of interferon is also available from Genzyme Corporation (Cambridge, Mass.).

Alternatively, a common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

In another embodiment, a peptide having a Der p III activity is screened for the ability to induce T cell non-responsiveness. The ability of a peptide known to stimulate T cells (as determined by one or more of the above described assays) to inhibit or completely block the activity of purified native Der p III or portion thereof and induce a state of non-responsiveness can be determined using subsequent attempts at stimulation of the T cells with antigen presenting cells that present native Der p III, or a peptide having a Der p III activity, following exposure to the peptide having a Der p III activity. If the T cells are unresponsive to the subsequent activation attempts, as determined by interleukin-2 synthesis and/or T cell proliferation, a state of non-responsiveness has been induced. See, e.g., Gimmi, et al. (1993) *Proc. Natl. Acad. Sci USA*, 90:6586-6590; and Schwartz (1990) *Science*, 248: 1349-1356, for assay systems that can be used as the basis for an assay in accordance with the present invention.

In yet another embodiment, peptides having a Der p III activity are identified by IgE binding activity. For therapeutic purposes, peptides of the invention preferably do not bind IgE specific for a house dust mite allergen or bind such IgE to a substantially lesser extent than the purified, native house dust mite allergen binds such IgE. Reduced IgE binding activity refers to IgE binding activity that is less than that of purified, native Der p III protein. If a peptide having a Der p III activity is to be used as a diagnostic reagent, it is not necessary that the peptide have reduced IgE binding activity compared to the native Der p III allergen. IgE binding activity of peptides can be determined, for example, by an enzyme-linked immunosorbent assay (ELISA) using, for example, sera obtained from a subject (i.e., an allergic subject) that has been previously exposed to the native Der p III allergen. Briefly, the peptide suspected of having a Der p III activity is coated onto wells of a microtiter plate. After washing and blocking the wells, antibody solution consisting of the plasma of an allergic subject who has been exposed to a peptide suspected of having a Der p III activity is incubated in the wells. The plasma is generally depleted of IgG before incubation. A labeled secondary antibody is added to the wells and incubated. The amount of IgE binding is then quantified and compared to the amount of IgE bound by a purified, native Der p III protein. Alternatively, the IgE binding activity of a peptide can be determined by Western blot analysis. For example, a peptide suspected of having a Der p III activity is run on a polyacrylamide gel using SDS-PAGE. The peptide is then transferred to nitrocellulose and subsequently incubated with sera from an allergic subject. After incubation with a labeled secondary antibody, the amount of IgE bound is then determined and quantified.

Another assay which can be used to determine the IgE binding activity of a peptide is a competition ELISA assay. Briefly, an IgE antibody pool is generated by combining plasma from house dust mite allergic subjects that have been shown by direct ELISA to have IgE reactive with native Der p III. This pool is used in ELISA competition assays to compare IgE binding of native Der p III and a peptide suspected of having a Der p III activity. IgE binding for the native Der p III and a peptide suspected of having a Der p III activity is determined and quantified.

If a peptide having an activity of Der p III binds IgE and is to be used as a therapeutic agent, it is preferable that such binding does not result in the release of mediators (e.g., histamines) from mast cells or basophils. To determine whether a peptide which binds IgE results in the release of mediators, a histamine release assay can be performed using standard reagents and protocols obtained from Amac, Inc. (Westbrook, Me.). Briefly, a buffered solution of a peptide suspected of having a Der p III activity is combined with an equal volume of whole heparinized blood from an allergic subject. After mixing and incubation, the cells are pelleted and the supernatants are processed and analyzed using a radioimmunoassay to determine the amount of histamine released.

Peptides having an activity of Der p III which are to be used as therapeutic agents are preferably tested in mammalian models of house dust mite atopy, such as the mouse model disclosed in Tamura et al., (1986) *Microbiol. Immunol.* 3:883-896, or in U.S. Pat. No. 4,939,239, or in the primate model disclosed in Chiba et al., (1990) *Int. Arch. Allergy Immunol.* 93:83-88. Initial screening for IgE binding to a peptide having an activity of Der p III may be performed by scratch tests or intradermal skin tests on laboratory animals or human volunteers, or in in vitro systems such as RAST, RAST inhibition, ELISA assay, RIA (radioimmunoassay), or a histamine release assay, as described above.

It is possible to modify the structure of a peptide having an activity of Der p III for such purposes as increasing solubility, enhancing therapeutic or prophylactic efficacy, or stability (e.g., shelf life ex vivo and resistance to proteolytic degradation in vivo). Such modified peptides are considered functional equivalents of peptides having an activity of Der p III as defined herein. A modified peptide can be produced in which the amino acid sequence has been altered, such as by amino acid substitution, deletion, or addition, to modify immunogenicity and/or reduce allergenicity, or to which a component has been added for the same purpose.

For example, a peptide having an activity of Der p III can be modified so that it maintains the ability to induce T cell non-responsiveness and bind MHC proteins without the ability to induce a strong proliferative response or, possibly, any proliferative response when administered in immunogenic form. In this instance, critical binding residues for T cell receptor function can be determined using known techniques (e.g., substitution of each residue and determination of the presence or absence of T cell reactivity). Those residues shown to be essential for interaction with the T cell receptor can be modified by replacing the essential amino acid with another, preferably similar amino acid residue (a conservative substitution) whose presence is shown to enhance, diminish but not eliminate, or not affect T cell reactivity. In addition, those amino acid residues which are not essential for T cell receptor interaction can be modified by being replaced by another amino acid whose incorporation may enhance, diminish but not eliminate, or not affect T cell reactivity, but whose incorporation does not eliminate binding to relevant MHC.

Additionally, a peptide having an activity of Der p III can be modified by replacing an amino acid shown to be essential for interaction with the MHC protein complex with another, preferably similar amino acid residue (conservative substitution) whose presence is shown to enhance, diminish but not eliminate or affect T cell activity. In addition, amino acid residues which are not essential for interaction with the MHC protein complex but which still bind the MHC protein complex can be modified by being replaced by another amino acid whose incorporation may enhance, not affect, or diminish but not eliminate T cell reactivity. Preferred amino acid substitutions for non-essential amino acids include, but are not limited to substitutions with alanine, glutaric acid, or a methyl amino acid.

Another example of modification of a peptide having an activity of Der p III is substitution of cysteine residues preferably with alanine, serine, threonine, leucine or glutamic acid residues to minimize dimerization via disulfide linkages. In addition, amino acid side chains of peptides of the invention can be chemically modified. Another modification is cyclization of the peptide.

In order to enhance stability and/or reactivity, a peptide having an activity of Der p III can be modified to incorporate one or more polymorphisms in the amino acid sequence of the protein allergen resulting from any natural allelic variation. Additionally, D-amino acids, non-natural amino acids, or non-amino acid analogs can be substituted or added to produce a modified protein within the scope of this invention. Furthermore, a peptide having an activity of Der p III can be modified using polyethylene glycol (PEG) according to the method of A. Sehon and co-workers (Wie et al., supra) to produce a protein conjugated with PEG. In addition, PEG can be added during chemical synthesis of the protein. Other modifications of a peptide having an activity of Der p III include reduction/alkylation (Tarr, *Methods of Protein Microcharacterization*, J. E. Silver ed., Humana Press, Clifton N.J. 155-194 (1986)); acylation (Tarr, supra); chemical coupling to an appropriate carrier (Mishell and Shiigi, eds., *Selected Methods in Cellular Immunology*, W H Freeman, San Francisco, Calif. (1980), U.S. Pat. No. 4,939,239; or mild formalin treatment (Marsh (1971), *Int. Arch. of Allergy and Appl. Immunol.* 41:199-215).

To facilitate purification and potentially increase solubility of a peptide having an activity of Der p III, it is possible to add an amino acid fusion moiety to the peptide backbone. For example, hexa-histidine can be added to the protein for purification by immobilized metal ion affinity chromatography (Hochuli, E. et al., (1988) *Bio/Technology* 6:1321-1325). In addition, to facilitate isolation of peptides free of irrelevant sequences, specific endoprotease cleavage sites can be introduced between the sequences of the fusion moiety and the peptide. In order to successfully desensitize a subject to Der p III protein or related allergen, it may be necessary to increase the solubility of the protein by adding functional groups to the protein or by omitting hydrophobic regions of the protein.

To potentially aid proper antigen processing of T cell epitopes within Der p III, canonical protease sensitive sites can be engineered between regions, each comprising at least one T cell epitope via recombinant or synthetic methods. For example, charged amino acid pairs, such as KK or RR, can be introduced between regions within a protein or fragment during recombinant construction thereof. The resulting peptide can be rendered sensitive to cleavage by cathepsin and/or other trypsin-like enzymes which would generate portions of the protein containing one or more T cell epitopes. In addition, such charged amino acid residues can result in an increase in the solubility of the peptide.

Site-directed mutagenesis of a nucleic acid encoding a peptide having an activity of Der p III can be used to modify the structure of the peptide by methods known in the art. Such methods may, among others, include polymerase chain reaction (PCR) with oligonucleotide primers bearing one or more mutations (Ho et al., (1989) *Gene* 77:51-59) or total synthesis of mutated genes (Hostomsky, Z. et al., (1989) *Biochem.*

*Biophys. Res. Comm* 161: 1056-1063). To enhance recombinant protein expression, the aforementioned methods can be applied to change the codons present in the cDNA sequence of the invention to those preferentially utilized by the host cell in which the recombinant protein is being expressed (Wada et al, supra).

Another aspect of the invention pertains to an antibody specifically reactive with a peptide having an activity of Der p III. The antibodies of this invention can be used to standardize allergen extracts or to isolate the naturally-occurring or native form of Der p III. For example, by using peptides having an activity of Der p III based on the cDNA sequence of Der p III, anti-protein/anti-peptide antisera or monoclonal antibodies can be made using standard methods. A mammal such as a mouse, a hamster or a rabbit can be immunized with an immunogenic form of the peptide (e.g., Der p III protein or an antigenic fragment which is capable of eliciting an antibody response). Techniques for conferring immunogenicity on a protein or peptide include conjugation to carriers or other techniques are well known in the art. A peptide having an activity of Der p III can be administered in the presence of adjuvant. The progress of immunization can be monitored by detection of antibody titers in plasma or serum. Standard ELISA or other immunoassays can be used with the immunogen as antigen to assess the levels of antibodies.

Following immunization, anti-Der p III antisera can be obtained and, if desired, polyclonal anti-Der p III antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, for example the hybridoma technique originally developed by Kohler and Milstein, (*Nature* (1975) 256:495-497) as well as other techniques such as the human B cell hybridoma technique (Kozbar et al., *Immunology Today* (1983) 4:72) and the EBV-hybridoma technique to produce human monoclonal antibodies (Cole et al., *Monoclonal Antibodies and Cancer Therapy* (1985) Alan R. Liss, Inc. pp. 77-96). Hybridoma cells can be screened immunochemically for production of antibodies specifically reactive with a peptide having an activity of Der p III and the monoclonal antibodies isolated.

The term antibody as used herein is intended to include fragments thereof which are also specifically reactive with a peptide having an activity of Der p III. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-Der p III portion.

Another aspect of this invention provides T cell clones and soluble T cell receptors specifically reactive with a peptide having an activity of Der p III. Monoclonal T cell populations (i.e., T cells genetically identical to one another and expressing identical T cell receptors) can be derived from a subject sensitive to Der p III, followed by repetitive in vitro stimulation with a Der p III protein or peptide having an activity of Der p III in the presence of MHC-matched antigen-presenting cells. Single Der p III MHC responsive cells can then be cloned by limiting dilution and permanent lines expanded and maintained by periodic in vitro restimulation. Alternatively, Der p III specific T-T hybridomas can be produced by a technique similar to B cell hybridoma production. For example, a mammal, such as a mouse, is immunized with a peptide having an activity of Der p III, T cells from the mammal can be purified and fused with an autonomously growing T cell tumor line. From the resulting hybridomas, cells responding to a peptide having an activity of Der p III are selected and cloned. Procedures for propagating monoclonal T cell populations are described in *Cellular and Molecular Immunology* (Abul K. Abbas et al., ed.), W.B. Saunders Company, Philadelphia, Pa. (1991) page 139. Soluble T cell receptors specifically reactive with a peptide having an activity of Der p III can be obtained by immunoprecipitation using an antibody against the T cell receptor as described in *Immunology: A Synthesis* (Second Edition), Edward S. Golub et al., ed., Sinauer Associates, Inc., Sunderland, Mass. (1991) pages 366-369.

T cell clones specifically reactive with a peptide having an activity of Der p III can be used to isolate and molecularly clone the gene encoding the relevant T cell receptor. In addition, a soluble T cell receptor specifically reactive with a peptide having an activity of Der p III can be used to interfere with or inhibit antigen-dependent activation of the relevant T cell subpopulation, for example, by administration to a subject sensitive to Der p III. Antibodies specifically reactive with such a T cell receptor can be produced according to the techniques described herein. Such antibodies can be used to block or interfere with the T cell interaction with peptides presented by MHC.

Exposure of allergic subjects to peptides having an activity of Der p III and which have T cell stimulating activity may cause the appropriate T cell subpopulations to become nonresponsive to the respective protein allergen (e.g., fail to stimulate an immune response upon such exposure). In addition, such administration may modify the lymphokine secretion profile as compared with exposure to the naturally-occurring protein allergen or portion thereof (e.g., result in a decrease of IL-4 and/or an increase in IL-2). Furthermore, exposure to peptides having an activity of Der p III which have T cell stimulating activity may influence T cell subpopulations which normally participate in the response to the allergen such that these T cells are drawn away from the site(s) of normal exposure to the allergen (e.g., nasal mucosa, skin, and lung) towards the site(s) of therapeutic administration of the protein or fragment derived therefrom. This redistribution of T cell subpopulations may ameliorate or reduce the ability of a subject's immune system to stimulate the usual immune response at the site of normal exposure to the allergen, resulting in a diminution in allergic symptoms.

A peptide having an activity of Der p III when administered to a subject sensitive to house dust mites is capable of modifying the B cell response, T cell response, or both the B cell and the T cell response of the subject to the allergen. As used herein, modification of the allergic response of a subject to a house dust mite allergen can be defined as non-responsiveness or diminution in symptoms to the allergen, as determined by standard clinical procedures (See e.g., Varney et al., (1990) *British Medical Journal* 302:265-269), including diminution in house dust mite induced asthmatic symptoms. As referred to herein, a diminution in symptoms includes any reduction in the allergic response of a subject to the allergen following a treatment regimen with a peptide of the invention. This diminution in symptoms may be determined subjectively (e.g., the subject feels more comfortable upon exposure to the allergen), or clinically, such as with a standard skin test.

Peptides or antibodies of the present invention can also be used for detecting and diagnosing sensitivity to Der p III. For example, this could be done by combining blood or blood products obtained from a subject to be assessed for sensitivity with a peptide having an activity of Der p III, under conditions appropriate for binding of components in the blood (e.g., antibodies, T cells, B cells) with the peptide(s) and determining the extent to which such binding occurs. Other diagnostic methods for allergic diseases which the peptides or antibodies of the present invention can be used include radio-allergosorbent test (RAST), paper radioimmunosorbent test (PRIST), enzyme linked immunosorbent assay (ELISA), radio immunoassays (RIA), immuno-radiometric assays (IRMA), luminescence immunoassays (LIA), histamine release assays and IgE immunoblots.

In another assay, the presence in a subject of IgE specific for Der p III and the ability of T cells of the subject to respond to T cell epitopes of Der p III can be determined by administering to the subject an Immediate Type Hypersensitivity test and/or a Delayed Type Hypersensitivity test (see e.g., *Immunology* (1985) Roitt, I. M., Brostoff, J., Male, D. K. (eds.), C. V. Mosby Co., Gower Medical Publishing, London, N.Y., pp. 19.2-19.18; pp. 22.1-22.10) utilizing a peptide having an activity of Der p III, or a modified form of a peptide having an activity of Der p III, each of which binds IgE specific for the allergen. The same subjects are administered a Delayed Type Hypersensitivity test prior to, simultaneously with, or subsequent to administration of the Immediate Type Hypersensitivity test. Of course, if the Immediate Type Hypersensitivity test is administered prior to the Delayed Type Hypersensitivity test, the Delayed Type Hypersensitivity test would be given to those subjects exhibiting a specific Immediate Type Hypersensitivity reaction. The Delayed Type Hypersensitivity test utilizes a peptide having an activity of Der p III which has human T cell stimulating activity and which does not bind IgE specific for the allergen in a substantial percentage of the population of subjects sensitive to the allergen (e.g., at least about 75%). Those subjects found to have both a specific Immediate type Hypersensitivity reaction and a specific Delayed Type Hypersensitivity reaction are administered an amount of a composition suitable for pharmaceutical administration. The composition comprises the peptide having an activity of Der p III as used in the Delayed Type Hypersensitivity test and a pharmaceutically acceptable carrier or diluent.

A peptide having an activity of Der p III can be used in methods of treating and preventing allergic reactions to a house dust mite allergen or a cross-reactive protein allergen. Thus, the present invention provides compositions suitable for pharmaceutical administration comprising an amount of at least one peptide having an activity of Der p III and a pharmaceutically acceptable carrier. Administration of the compositions of the present invention to a subject to be desensitized can be carried out using known procedures, at dosages and for periods of time effective to reduce sensitivity (i.e., reduce the allergic response) of the subject to house dust mite. The term subject is intended to include living organisms in which an immune response can be elicited, e.g., mammals. Examples of subjects include humans, dogs, cats, mice, rats, and transgenic species thereof. An amount of at least one peptide having an activity of Der p III necessary to achieve a therapeutic effect may vary according to factors such as the degree of sensitivity of the subject to house dust mite, the age, sex, and weight of the subject, and the ability of a peptide having an activity of Der p III to elicit an antigenic response in the subject. Dosage regima may be adjusted to provide the optimum therapeutic response. For example, several divided doses may be administered daily or the dose may be proportionally reduced as indicated by the exigencies of the therapeutic situation.

The active compound (i.e., at least one peptide having an activity of Der p III) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

To administer a peptide having an activity of Der p III by other than parenteral administration, it may be necessary to coat the peptide with, or co-administer the peptide with, a material to prevent its inactivation. For example, a peptide having an activity of Der p III may be administered to a subject in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., (1984) *J. Neuroimmunol.* 7:27). For purposes of inducing T cell non-responsiveness, the composition is preferably administered in non-immunogenic form, e.g., one that does not contain adjuvant.

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating active compound (i.e., at least one peptide having an activity of Der p III) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., at least one peptide having an activity of Der p III) plus any additional desired ingredient from a previously sterile-filtered solution thereof.

When the peptide having an activity of Der p III is suitably protected, as described above, the peptide may be orally administered, for example, with an inert diluent or an assimilable edible carrier. The peptide and other ingredients may also be enclosed in a hard or soft shell gelatin capsule, compressed into tablets, or incorporated directly into the subject's diet. For oral therapeutic administration, the active compound may be incorporated with excipients and used in the form of ingestible tablets, buccal tablets, troches, capsules, elixirs, suspensions, syrups, wafers, and the like. The percentage of the active ingredient in the compositions and preparations may, of course, be varied and may conveniently be between about 5 to about 80% of the weight of the unit. The amount of active compound in such therapeutically useful compositions is such that a suitable dosage will be obtained.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the compositions suitable for pharmaceutical administration is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in subjects.

The invention also provides a composition comprising at least two peptides having an activity of Der p III (e.g., a physical mixture of at least two peptides), each having T cell stimulating activity. Alternatively, a peptide having at least two regions, each having T cell stimulating activity (i.e., each region comprising at least one T cell epitope) can be administered to an allergic subject. A composition of two peptides having a Der p III activity or a composition of two peptides having at least two regions, each having T cell stimulating activity can be administered to a subject in the form of a composition with a pharmaceutically acceptable carrier as hereinbefore described. An amount of one or more of such compositions can be administered simultaneously or sequentially to a subject sensitive to a house dust mite allergen to treat such sensitivity.

The cDNA (or the mRNA which served as a template during reverse transcription) encoding a peptide having an activity of Der p III can be used to identify similar nucleic acids in any variety or type of animal and, thus, to molecularly clone genes which have sufficient sequence homology to hybridize to the cDNA encoding a peptide having an activity of Der p III. Thus, the present invention includes not only peptides having an activity of Der p III, but also other proteins which may be allergens encoded by DNA which hybridizes to DNA of the present invention.

Isolated peptides that are immunologically related to Der p III, such as by antibody cross-reactivity or T cell cross-reactivity, other than those already identified, are within the scope of the invention. Such peptides bind antibodies specific for the protein and peptides of the invention, or stimulate T cells specific for the protein and peptides of this invention.

A peptide having an activity of Der p III (i.e., Der p III produced recombinantly or by chemical synthesis) is free of all other house dust mite proteins and, thus, is useful in the standardization of allergen extracts which are key reagents for the diagnosis and treatment of house dust mite hypersensitivity. In addition, such a peptide is of a consistent, well-defined composition and biological activity for use in preparations that will be administered for therapeutic purposes (e.g., to modify the allergic response of a subject sensitive to house dust mite). Such peptides can also be used to study the mechanism of immunotherapy of D. pteronyssinus allergy and to design modified derivatives or analogs useful in immunotherapy.

Work by others has shown that high doses of allergen extracts generally produce the best results during immunotherapy (i.e., best symptom relief). However, many subjects are unable to tolerate large doses of such extracts due to systemic reactions elicited by the allergens and other components within these preparations. A peptide having an activity of Der p III has the advantage of being free of all other mite protein. Thus, such a peptide can be administered for therapeutic purposes with fewer anticipated side effects.

It is now also possible to design an agent or a drug capable of blocking or inhibiting the ability of a house dust mite allergen to induce an allergic reaction in sensitive subjects. Such agents could be designed, for example, in such a manner that they would bind to relevant anti-Der p III IgE molecules, thus preventing IgE-allergen binding, and subsequent mast cell/basophil degranulation. Alternatively, such agents could bind to cellular components of the immune system, resulting in suppression or desensitization of the allergic responses to house dust mite allergens. A non-restrictive example of this is the use of peptides including B or T cell epitopes of Der p III or modifications thereof, based on the cDNA protein structure of Der p III to suppress the allergic response to a house dust mite allergen. This could be carried out by defining the structures of fragments encoding B and T cell epitopes which affect B and T cell function in in vitro studies with blood components from subjects sensitive to house dust mite.

The invention is further illustrated by the following examples which should not be construed as further limiting the subject invention. The contents of all references and published patent applications cited throughout this application are hereby incorporated by reference.

The following methodology was used throughout the Examples.

EXAMPLES

Materials and Methods

*D. pteronyssinus* Cultures

Whole mites were purchased from the Commonwealth Serum Laboratories, Parkville, Australia and spent medium was a gift from the same source.

Purification of Native Der p III

Using a method adapted from Heymann et al. (Heymann et al. *J Allergy Clin Immunol* (1989) 83: 1055-1067), 15 ml of a 50-80% saturated ammonium sulfate precipitate of *D. pteronyssinus* spent growth medium was applied to an upward flowing, 2 cm×90 cm polyacrylamide P-100 column equilibrated in PBS (Pharmacia, LKB Biotechnology, Uppsala, Sweden). The protein content of the eluted 5 ml fractions was determined by measuring optical density (A280 nm) and analysis by SDS-PAGE. Those fractions containing predominantly bands in the 30 kDa region were pooled, concentrated by polyethylene glycol 6000 (BDH Chemicals, Aust. PTY. Ltd. Kilsyth, Vic. Aust), dialyzed against PBS and passed over the column again. This was repeated twice until the analysis by SDS-PAGE determined that the only bands detectable were a doublet of approximately molecular weight 30 kDa.

Protein Sequence Analysis

The affinity purified native Der p III and Der f III proteins were subjected to HPEC using a 12% column system (Applied Biosystems, Foster City, Calif.). The affinity purified proteins or the HPEC fractions of the appropriate molecular weight were then subjected to protein sequence analysis using Applied Biosystems model 477A gas-phase sequenator with on-line phenylthiohydantoin derivative analysis (model 120). Alternatively, the affinity purified proteins were first separated by SDS-PAGE (BioRad), transferred to Problot (Applied Biosystems) and sequenced using a Beckman model LF300. After initial sequence analysis of the proteins, o-phthalaldehyde was applied to block N-termini except those with prolines (position 13 for Der p III) to eliminate contaminating peptide sequences and extend the N-terminal sequence unambiguously. The CNBr peptides were produced by cleaving the affinity purified proteins with 2% (w/v) CNBr in 70% (w/v) formic acid overnight at room temperature. The digested peptides were subjected to HPEC for purification and then the peptide fragments were subjected to sequence analysis.

Preferred Codon Usage

The codon usage bias for the mature proteins Der f I (Dilworth et al. *Clin Exp Allergy* (1991) 21:25-32), Der f II (Trudinger et al. *Clin Exp Allergy* (1991) 21:33-37), Der p I (Chua et al. *J Exp Med* (1988) 167:175-182) and Der p II (Chua et al. *Int Arch Allergy Appl Immunol* (1990) 21:118-123) was determined. The average percent usage of each triplet codon for each amino acid was determined for each of these four *Dermatophagoides* proteins and the results tabulated in Table 1.

TABLE 1

Preferred codon usage table for Dermatophagoides allergens.

| Amino acid | | Codon | % |
|---|---|---|---|
| Ala | A | GCT | 45.4 |
| | | GCC | 33 |
| | | GCA | 21.6 |
| | | GCG | 0 |
| Cys | C | TGT | 55.2 |
| | | TGC | 44.8 |
| Asp | D | GAT | 92.3 |
| | | GAC | 7.7 |
| Glu | E | GAA | 100 |
| | | GAG | 0 |
| Phe | F | TTC | 82.5 |
| | | TTT | 17.5 |
| Gly | G | GGT | 65.2 |
| | | GGA | 24.5 |
| | | GGC | 10.3 |
| | | GGG | 0 |
| His | H | CAT | 78.8 |
| | | CAC | 21.2 |
| Ile | I | ATT | 50 |
| | | ATC | 48.5 |
| | | ATA | 1.5 |
| Lys | K | AAA | 99 |
| | | AAG | 1 |
| Leu | L | TTG | 64.5 |
| | | TTA | 18.5 |
| | | CTC | 8 |
| | | CTT | 6.5 |
| | | CTG | 2.5 |
| | | CTA | 0 |
| Met | M | ATG | 100 |
| Asn | N | AAT | 52 |
| | | AAC | 48 |
| Pro | P | CCA | 87.2 |
| | | CCC | 9.6 |
| | | CCG | 3.2 |
| | | CCT | 0 |
| Gln | Q | CAA | 94.4 |
| | | CAG | 5.6 |
| Arg | R | CGA | 36.5 |
| | | CGT | 41.6 |
| | | CGC | 16.5 |
| | | AGA | 5.4 |
| | | CGG | 0 |
| | | AGG | 0 |
| Ser | S | TCA | 42.5 |
| | | TCT | 18.4 |
| | | AGT | 11.2 |
| | | TCG | 11.2 |
| | | AGC | 10.2 |
| | | TCC | 6.5 |
| Thr | T | ACT | 39.2 |
| | | ACA | 35 |
| | | ACC | 18.9 |
| | | ACG | 6.9 |
| Val | V | GTT | 51.2 |
| | | GTC | 33.8 |

TABLE 1-continued

Preferred codon usage table for Dermatophagoides allergens.

| Amino acid | Codon | % |
|---|---|---|
|  | GTA | 12.3 |
|  | GTG | 2.7 |
| Trp W | TGG | 100 |
| Tyr Y | TAT | 62 |
|  | TAC | 38 |
| Stop | TAA | 75 |
|  | TGA | 25 |
|  | TAG | 0 |

Construction of the D. pteronyssinus λ gt10 cDNA Library

Polyadenylated mRNA (10 μg) was used to synthesize cDNA by the RNase H method (Gubler et al. *Gene* (1983) 25:263-269) using a kit (Amersham International, Aylesbury, U.K.). After the addition of EcoRI restriction enzyme linkers (New England Biolabs, Beverly, U.S.A.), the cDNA was ligated to alkaline-phosphatase treated lambda gt10 arms (Promega Biotec, Madison, Wis.). The recombinant phage DNA was packaged and plated out in *E. coli* JP777 to produce a library of 5×10$^5$ recombinants.

Kinase End-Labeling of Oligonucleotides

Oligonucleotides were synthesized using an Applied Biosystem PCR mate (Applied Biosystems, Foster City, Calif.). Twenty picomole of oligonucleotide DNA was end labeled with (γ-$^{32}$P) ATP using T4 polynucleotide kinase (Promega Corp., Madison, Wis.) (Maniatis, T., Fritsch, E. F. and Sambrook, *J. Molecular Cloning: A Laboratory Manual.* 2nd Ed. Cold Spring Harbor Laboratory Press, 1989). Labeled oligonucleotide was purified by 15% polyacrylamide gel electrophoresis and subsequently eluted into sterile distilled water.

Isolation of Der p III cDNA Clones from the λ gt10 cDNA Library

Screening of the library was performed with two probes designed using both N-terminal and internal protein sequence data obtained as described above for the group III allergens. The first, P3forward3 (P3F3), was a 38 mer in length with the following nucleotide sequence, 5'TCAGAAAAAGCTTTG-GCTGGTGAATCACCATATCAAAT 3' (SEQ ID NO:8). The second probe, P3reverse4(P3R4), a 41 mer with the following nucleotide sequence, 5'GAATCAACACCACCATT-AGCAACATCACCACCGCAAATCAT3' (SEQ ID NO:9). The library was plated at 25,000 pfu per 150 mm petri dish and the phage were lifted onto nitrocellulose (Schleicher & Schuell, Dassel, Germany). Duplicate filter lifts from each plate were denatured and baked for hybridization with a different one of the two probes (Maniatis, T., Fritsch, E. F. and Sambrook, J. *Molecular Cloning: A Laboratory Manual.* 2nd Ed. Cold Spring Harbor Laboratory Press, 1989). Hybridizations were performed in hybridization mix (6× sodium chloride/sodium citrate pH 7.0 (SSC), 0.1% Denhardts, 100 μg/ml denatured herring sperm DNA) at 42° C. with 10$^6$ cpm/ml labeled probe overnight. Filters were washed three times at 42° C. for 20 min and then at 50° C. for 10 min, in 400 ml wash solution containing 6×SSC, 0.1% Triton X-100.

Isolation of DNA from λgt10 Der p III Clones

Phage DNA from the Der p III clones was prepared using a polyethylene glycol precipitation procedure (Chua et al., *J Exp Med* (1988) 167:175-182).

Subcloning and DNA Sequencing

Purified Der p III phage DNA was digested with EcoRI restriction enzyme (Toyobo) and the released fragment ligated to EcoRI restriction enzyme digested M13mp19 sequencing vector (Messing, *Meth. Enzymol.* (1983) 101: 20-78). The recombinant DNA was transformed using *E. coli* TG-1 and sequencing performed using the dideoxynucleotide chain termination method and Sequenase (U.S. Biochemicals) (Sanger et al., *Proc Natl Acad Sci USA* (1977) 74:5463-5467). The oligonucleotide primers used for sequencing included the universal primers, a 7-mer sequencing primer (−40)5' CAGCACTGACCCTTTTG3' (SEQ ID NO:4) and a 16-mer reverse sequencing primer (−24)5' AACAGC-TATGACCATG3' (SEQ ID NO: 5), the two internal primers used for the library screening (SEQ ID NOS: 8 and 9) and two internal primers P3forward5(P3F5) 5'AAAGCTGTTGGATTACCA3' (SEQ ID NO:6) and P3reverse5(P3R5) 5'TACATCCGATCCTTTTGC3' (SEQ ID NO:7) and P3F4 5'GCGGATCCATTGTTG-GTGGT 3' (SEQ ID NO: 18). The two internal probes were designed to correspond to nucleotide residues 456-473 (P3F5) and 491-474 (P3R5) (FIG. 1.). The primers were used to sequence the isolated clone in both orientations.

DNA and Protein Sequence Analysis

Sequence analysis was performed using the MAC VECTOR software (IBI, New Haven, U.S.A.). Computation for sequence homology with other proteins was performed at the NCBI using the BLAST network service. The version of BLAST used was BLAST 1.3.1OMP (7 Jul. 1993).

Example 1

Sequence of the Native Group III Allergens

The protein isolation procedure produced a Der p III sample which ran as a doublet with molecular weights 30 and 28 k when analyzed by SDS-PAGE. Both bands reacted with polyclonal mouse anti-Der f III in accord with the interspecies cross-reactivity previously reported (Thomas et al., *Exp. Appl. Acarol.* (1992) 16:153-164). Der f III isolated from a 5A12 monoclonal antibody (Heymann et al. *J. Allergy Clin. Immun.* (1989) :1055-1067) column exhibited similar characteristics. Using the o-pthalaldehyde to eliminate the contaminating protein sequences, the N-terminal sequencing of both native Der p III and Der f III corrected and extended the known Der p III sequence and extended the Der f III sequence. The Der p III N-terminal sequence was extended to IVGGEKALAGQSPYQISLQSSSHFSGGTIL (SEQ ID NO:16). The Der f III N-terminal sequence was extended to IVGGVKAKAGDSPYQISLQSSSHFXGGSILD (SEQ ID NO: 15). Comparison of the sequence data published by Stewart et al. (*Immunology* (1992) 75: 29-35) and Heymann et al., (*J. Allergy. Clin. Immunol* (1989) 83: 1055-1067) for the group III allergens with the data herein indicated several errors in the published sequence. In particular, a non-conservative change at residue 8 from a positively charged lysine to a non-polar hydrophobic leucine was found (Der f III, Heymann et al., *J Allergy Clin Immunol* (1989) 83: 1055-1067).

Two internal peptides of Der f III were isolated by HPEC after CNBr digestion of the natural protein, MICGGDVANG-GVDSEQGD (SEQ ID NO: 10) and MTLDQTNAKPV-PLPTS (SEQ ID NO:12).

Example 2

Sequence of Recombinant Der p III

The protein sequence information obtained as described in Example 1 was used in conjunction with the preferred codon usage data (Table 1) to construct two oligonucleotides probes. These oligonucleotides were designed to hybridize to nucleotide residues 159-196 and to residues 688-648 of the Der p III clone (FIG. 2). Only clones which hybridized strongly with both probes were isolated from the λ gt10 cDNA library. The resulting nucleotide sequence for the P3WS1 clone and the deduced amino acid sequence is shown in FIG. 1. The complete nucleotide sequence was 1059 bp in length. This includes a 5' non-coding region of 62 bp, a 211bp 3' untranslated region and an open reading frame of 786 bp with a stop codon (TGA) at nucleotide residues 846-848. There is no poly A tail but there does appear to be a polyadenylation signal (AATAAA). The open reading frame encodes a protein which includes a 29 amino acid pre-pro region and starting at the N-terminal isoleucine, a mature protein of 232 amino acid residues with a calculated molecular weight of 24,985 and pI of 8.5. The methionine residue (ATG) at amino acid position –29 is the most likely translation initiation site. Selection for this initiation site was based in part on the presence of a sequence following the methionine which encodes a classical signal peptide of 18 amino acid residues with predominantly hydrophobic residues present. In addition, the immediate sequence prior to this ATG codon, 5'GAAAGATG3', conforms loosely to the Kozak consensus sequence (CCAC-CATG) for the eucaryotic translation initiation site with the crucial purine (most often A) at the –3 position (Kozak, *Nucleic Acid Research* (1984) 12:857-872).

The protein sequencing data of Der p III described in Example 1 differs from the amino acid sequence deduced from the cDNA of the P3WS1 clone as a result of the substitutions of Glu/Gln at residue 11 and a possible Cys/Ser substitution at residue 17. These substitutions may be due to the existence of Der p III in different isoforms. Analysis of the deduced protein sequence for Der p III P3WS 1 confirmed that the position of the Der f III CNBr peptide 1 (MI(C) GGDVANGGVDS(E)QGD) (SEQ ID NO:10) was correctly predicted to be from amino acid residues 177-183 and has 88% identity with the recombinant sequence in this region, MICGGDVANGGKDSCQD (SEQ ID NO: 11). Interestingly, there are two identical non-conservative changes that exist when the native Der f III peptide sequence is aligned with the P3WS1 clone sequence. There is a change from a non-polar hydrophobic valine at 178 (according to numbering in FIG. 1) in Der f III to a positively charged lysine residue in the P3WS1 clone sequences. The other change is a glutamic acid residue at 181 in the Der f III substituted for a cysteine residue in the P3WS 1 clone sequence. The cysteine forms one of the disulfide bridges in both these and most other trypsin proteins. The predicted alignment of the second Der f III peptide, (M)TLDQTNA(K)PVPL(P)(T)(S) (SEQ ID NO:12), produced by the CNBr digestion was from amino acid residues 95-110 (MKLNQKNAKAVGLPAK) (SEQ ID NO: 13). There is 63% homology with the P3WS1 clone in this region. These differences between the Der p III and Der f III protein sequences are consistent with the 20% sequence variation found between other homologous allergens from this species such as the Der p I and Der f I; and Der p II and Der f II.

The complete sequence for the Der p III P3 WS1 clone encodes a protein of 319 amino acids. Der p III, like all known trypsins, is synthesized as a pre-pro zymogen. The cleavage site of the signal peptide is postulated to be between amino acid residues –12 and –11 as the residues around this site conform to the amino acid constraints outlined by von Heijne, (von Heijne, *Eur J Biochem* (1983) 133:17-21). Von Heijne proposed that small neutral amino acids are strongly preferred at positions –1 and –3 from the cleavage site, such as the alanine and tyrosine seen in the Der p III gene. Proline residues are never found in positions +1 to –3 thus excluding any other sites. Most mammalian trypsin proteins have been reported to have pre or signal peptides of 15 or 16 amino acids. The Der p III peptide is 18 amino acids in length. While the difference in length is relatively small, it does seem that the length of the signal peptide may be attributable to the phylogenetic diversity of the species from which the trypsin originated. This is most apparent in *Streptomyces griseus* with a 32 amino acid pre peptide (Kim et al., *Biochem Biophys Res Commun* (1991) 181:707-713). It has also been reported that for mammalian trypsins the signal peptide contains two specific clusters of two and then four hydrophobic residues (MacDonald et al., *J Biol Chem* (1982) 257:9724-9732; Le Huerou et al, *Eur J Biochem* (1990) 193:767-73). There is an abundance of hydrophobic residues within this region of the Der p III gene but they are not arranged into highly conserved clusters. The same is true of the signal peptides for both Drosophila melangastor (Davis et al., *Nucleic Acid Research* (1988) 13:6605-6615) and *S. griseus* (Kim et al., *Biochem Biophys Res Commun* (1991) 181:707-713). It is possible therefore that the highly conserved clusters of hydrophobic residues are not a characteristic of all trypsin proteins but rather that of mammalian trypsins.

Downstream from the signal peptide is the 11 residue pre-activation peptide from amino acid residues –11 to –1. Comparison of this pro region with other pro regions from trypsins of various species indicates the Der p III pro peptide is unusual. Both vertebrate and invertebrate trypsins have been shown to have an octapeptide and or a hexapeptide pro region with four contiguous aspartyl residues followed by a lysine residue at the –1 position (Le Huerou et al., *Eur J Biochem* (1990) 193:767-73). It is the carboxyl region of this lysine residue which is cleaved during the activation of the trypsinogen to trypsin. The Der p III lacks this polyaspartyl-lysine sequence. The trypsinogen therefore can not be activated by the usual mechanism. There are a few other trypsins which are similar to Der p III in this respect, *D. melangastor* (Davis et al., *Nucleic Acid Research* (1988) 13:6605-6615), *S. griseus* (Kim et al., *Biochem Biophys Res Commun* (1991) 181:707-713) and most interestingly, a 32 kDa anionic trypsin from the rat pancreas (Gendry and Launay, *Biochemica et Biophysica Acta* (1988) 955:243-249). This group showed that enterokinase, an enzyme which has a highly specific affinity for the polyaspartyl-lysine residues in trypsin proteins, had no effect on the trypsin that they isolated. They suggested therefore that a different mechanism was being used for the activation process. The absence of any homology of the Der p III proenzyme region with any of the known sequences may imply a unique activation mechanism.

A search of the protein database has confirmed that Der p III P3WS1 is homologous to both vertebrate and invertebrate trypsins. The Der p III allergen is not a mite chymotrypsin (Gendry and Launay, *Biochemica et Biophysica Acta* (1988) 955:243-249) as comparison of the N-terminal protein sequences showed that they differ by as much as 50%. FIG. 2 shows a comparison of the amino acid sequences of Der p III P3WS1 and crayfish trypsins (SEQ ID NOS: 2 and 3). The crayfish has 44% homology with Der p III. There are seven cysteine residues, six of these residues are known to form disulphide bridges, 54-70, 181-198 and 210-236 (FIG. 2.) (Hartley, *Phil Trans Roy Soc Lond B* (1970) 257:77-87). Most importantly, the Der p III protein contains the highly conserved residues involved in the catalytic activity and substrate specificity of the trypsin proteins. The conserved His 40 and Ser 185 (FIG. 1) represent the charge relay system which comprise the active catalytic site of the trypsin enzyme. The positively charged aspartic acid residue at 179, represents the trypsin specificity site. Most serine proteases have a neutral amino acid at this residue (Keil, *The Enzymes*. Academic Press, New York, 1971, pages 249-279). The glycine residues at 206 and 211 in combination with the aspartic acid at 179 are responsible for accommodating the bulky positively charged side chains of lysine and arginine, the substrate residues cleaved by trypsins. Amino acid residues 179-185 and 202-206 (FIG. 1) form the S1 binding pockets which are involved in the binding of the substrate to the trypsin molecule. The areas immediately surrounding all of these important residues are the most conserved regions of the Der p III protein. All these results are consistent with the fact that among trypsin proteins from different species structural variations occur in those regions of the molecule which are not important for catalytic activity (Vithayathil et al., *Arch Biochem Biophys* (1961) 92:532-540).

Most trypsin proteins generally have a common pairing of cysteine residues to form six disulphide bridges, with two of these bridges, Cys 15-145 and Cys 117-218 being unique to this group of proteins. Der p III like both crayfish (Titani et al., *Biochemistry* (1983) 22:1459-1465) and *S. griseus* are missing these two unique links, but more importantly Der p III is unique as it contains an extra unpaired cysteine residue. This residue may be the equivalent to Cys 15 in the bovine trypsin which unlike, Cys 145, 117 and 218 was not eliminated during evolutionary divergence of the mite trypsin.

The isolation of the gene encoding the nucleotide sequence for the group III allergen, Der p III is the first primary sequence determination for this group of *Dermatophagoides* allergens. Comparison of the sequence with other vertebrate and invertebrate serine proteases in view of substrate binding experiments (Stewart et al., *Immunology* (1992) 75:29-35; Ando et al., *Arerugi* (1992) 41:704-707), indicates that the group III allergens are trypsin proteins. Trypsin proteins are secreted as pre-pro zymogens by the pancreatic acinar cells of all vertebrate and invertebrate species. Invertebrate trypsins have been reported to have a molecular weight ranging from 20 to 30 kDa (Graf et al., *Insect Biochem* (1985) 15:611-618). The Der p III P3WS1 trypsinogen has a calculated molecular weight of 28 kDa and the corresponding mature protein a molecular weight of 24,985 kDa while the native protein purified, existed as duplicate of 28 and 30 kDa as estimated by SDS-PAGE. There have been other reports of multiple protein bands being isolated for both Der f III (Thomas et al, *Exp Appl Acarol* (1992) 16:153-164) and Der p III (Stewart et al., *Immunology* (1992) 75:29-35). These results are not unusual as trypsin proteins are known to exist in several isoforms. Gendry and Launay (1988) isolated duplicate protein bands of an anionic trypsin-like protein from rat pancreas. They demonstrated that the higher 32 kDa band represented the inactive trypsin and the lower 30 kDa band represented the active form of the trypsin which could autocatalyze the cleavage of the 32 kDa band. It is therefore possible that the 30 kDa band represents the inactive trypsinogen and the 28 kDa band the active trypsin. The number of isozymes for invertebrate trypsins has been reported to range from 1-12 (MacDonald et al. *J Biol Chem* (1982) 257:9724-9732). Stewart et al. (1992) proposed nine major isoforms of Der p III existed, with pI's ranging from 4 to >8.

Example 3

Expression and Purification of Recombinant Der p III

A complementary DNA insert encoding Der p III (FIG. 1) was digested with EcoRI and inserted into pUC 19. To remove the non-translated 5' sequence as well as part of the putative hydrophobic leader, the cDNA was cleaved with MscI and an EcoRI linker was added. Subsequently, the truncated Der p III fragment was EcoRI digested and subcloned into the expression vector pET11d (Studier et al., *Gene Expression Technology: Methods in Enzymology* 185, Academic Press, San Diego, Calif. (1990) 60-89). The sequence and reading frame were verified by DNA sequencing. The Der p III coding sequence encompassed residue 13 to the stop codon (see FIG. 1). The expression vector pET11d Der p III was transformed into the *E. coli* host strain BL21 (DE3) and selected on plates containing 150 µg/ml ampicillin (Studier et al., *Gene Expression Technology: Methods in Enzymology* 185, Academic Press, San Diego, Calif. (1990) 60-89). A single transformant colony was grown up in 2 ml volume of BHIB medium containing 150 µg/ml ampicillin at 37° C., for approximately 6 hr. Ten milliliters of this culture was spread onto a selection plate and grown overnight at 37° C. The bacterial lawn was recovered in 2 ml media and added to 500 ml of BHIB medium (150 µg/ml ampicillin) and grown at 37° C. to $A_{600}$=1.0. Recombinant expression was induced by the addition of IPTG to a final concentration of 1 mM. After 2 hr growth, cells were harvested, lysed and the proteins solubilized in 6 M guanidine HCl buffer containing 100 mM 2-ME as previously described for the ragweed recombinant allergens, Amb a I.1 and Amb a II (Rogers, et al. (1991) *J. Immunol,* 147:2547-2552).

The guanidine HCl lysate containing Der p III was subjected to $Ni^{2+}$ metal-ion affinity chromatography under denaturing conditions in 8 M urea (Hochuli, E. et al., (1988) *Bio/Technology* 6:1321-1325). After elution from the $Ni^{2+}$ chelating support, QIAGEN NTA-Agarose (Diagen GmH, Dusseldorf, Germany), the recombinant Der p III protein preparations were subjected to SDS-PAGE analysis (FIG. 3).

Recombinant Der p III had an expected molecular weight of approximately 27 kDa as predicted for the 252 amino acids plus amino acids used as a purification tag (MGHHHHHHEF (SEQ ID NO:17)). The pET11d expression system and the $Ni^{2+}$ methyl-ion-affinity chromatography method generated approximately 12 mg recombinant Der p III per liter of growth medium (as assessed by $A_{280}$ measurement). This expression and purification scheme yielded a protein preparation with purity exceeding 90% as assessed by SDS-PAGE visualized by Coomassie Blue staining. (FIG. 3). The observed apparent molecular weight of approximately 32 kDa is slightly higher than that predicted from the primary structure (FIG. 1, and above). In FIG. 3, increasing concentrations of Der p III preparation were examined to verify the purity (lane 1, 4.3 µg; lane 2, 8.7 µg; lane 3, 13.8 µg; lane 4, 17.4 µg; markers are indicated by M).

EQUIVALENTS

Those skilled in the art will recognize or be able to ascertain using no more than routine experimentation, numerous equivalents to the specific embodiments described herewith. Such equivalents are considered to be within the scope of this invention and are encompassed by the following claims.

What is claimed is:

1. An isolated peptide of a Der p III protein allergen consisting of a portion of the amino acid sequence of SEQ ID NO: 2 at least 30 amino acid residues in length, wherein the peptide is free of all other house dust mite proteins and has at least one of the following features: is capable of stimulating T or B cells specific for a Der p III protein allergen; or includes at least one B cell epitope recognized by a B cell receptor specific for a Der p III protein allergen and wherein the peptide does not comprise the amino acid sequence −29 to 232 or 1-232 of SEQ ID NO: 2.

2. The isolated peptide of claim 1, which is produced by recombinant expression of a nucleic acid.

3. The isolated peptide of claim 1, which is produced by chemical synthesis.

4. An isolated peptide of a Der p III protein consisting of a portion of the amino acid sequence of SEQ ID NO: 2 at least 30 amino acid residues in length, wherein the peptide is free of all other house dust mite proteins and wherein the peptide does not comprise the amino acid sequence −29 to 232 or 1-232 of SEQ ID NO: 2.

5. The isolated peptide of claim 4, consisting of a portion of the amino acid sequence of SEQ ID NO.: 2 at least 60 amino acid residues in length.

6. The isolated peptide of claim 4, consisting of a portion of the amino acid sequence of SEQ ID NO.: 2 at least 80 amino acid residues in length.

7. The isolated peptide of claim 4, consisting of a portion of the amino acid sequence of SEQ ID NO.: 2 at least 100 amino acid residues in length.

8. The isolated peptide of claim 1, consisting of a portion of the amino acid sequence of SEQ ID NO.: 2 at least 60 amino acid residues in length.

9. The isolated peptide of claim 1, consisting of a portion of the amino acid sequence of SEQ ID NO.: 2 at least 80 amino acid residues in length.

10. The isolated peptide of claim 1, consisting of a portion of the amino acid sequence of SEQ ID NO.: 2 at least 100 amino acid residues in length.

* * * * *

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
       (A) LENGTH: 1059 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 63..848

(ix) FEATURE:
       (A) NAME/KEY: mat_peptide
       (B) LOCATION: 150..848

(xi) SEQUENCE DESCRIPTION: SEQ ID NO: 1:

```
CTTTTTTTTT TTTTTTGAAA ACATTGAAAA ACATTGAAGC AACTGTGTGT ACAACCAGAA            60

AC ATG ATC ATC TAT AAT ATT TTA ATT GTT TTA TTA TTG GCC ATT AAT             107
   Met Ile Ile Tyr Asn Ile Leu Ile Val Leu Leu Leu Ala Ile Asn
   -29             -25                 -20                 -15

ACA TTG GCT AAT CCA ATT CTA CCA GCA TCA CCA AAT GCA ACT ATT GTT            155
Thr Leu Ala Asn Pro Ile Leu Pro Ala Ser Pro Asn Ala Thr Ile Val
                -10                 -5                  1

GGT GGT GAA AAA GCA TTA GCT GGT GAA TGT CCA TAT CAG ATT TCA TTA            203
Gly Gly Glu Lys Ala Leu Ala Gly Glu Cys Pro Tyr Gln Ile Ser Leu
        5                   10                  15

CAA TCA AGT AGT CAT TTT TGT GGT GGT ACT ATT CTT GAT GAA TAT TGG            251
Gln Ser Ser Ser His Phe Cys Gly Gly Thr Ile Leu Asp Glu Tyr Trp
    20                  25                  30

ATT TTA ACA GCT GCA CAT TGT GTT GCC GGA CAA ACA GCA AGT AAA CTT            299
Ile Leu Thr Ala Ala His Cys Val Ala Gly Gln Thr Ala Ser Lys Leu
35                  40                  45                  50

TCA ATT CGT TAC AAT AGT TTA AAA CAT TCA TTA GGT GGT GAA AAA ATT            347
Ser Ile Arg Tyr Asn Ser Leu Lys His Ser Leu Gly Gly Glu Lys Ile
                55                  60                  65

TCT GTT GCT AAA ATT TTT GCA CAT GAA AAA TAT GAT AGT TAT CAA ATT            395
Ser Val Ala Lys Ile Phe Ala His Glu Lys Tyr Asp Ser Tyr Gln Ile
            70                  75                  80

GAT AAT GAT ATT GCA TTG ATT AAG CTT AAA TCA CCT ATG AAA TTA AAT            443
Asp Asn Asp Ile Ala Leu Ile Lys Leu Lys Ser Pro Met Lys Leu Asn
        85                  90                  95

CAG AAA AAT GCC AAA GCT GTT GGA TTA CCA GCA AAA GGA TCG GAT GTA            491
Gln Lys Asn Ala Lys Ala Val Gly Leu Pro Ala Lys Gly Ser Asp Val
    100                 105                 110

AAA GTT GGT GAT CAA GTT CGT GTT TCT GGT TGG GGT TAT CTT GAA GAA            539
Lys Val Gly Asp Gln Val Arg Val Ser Gly Trp Gly Tyr Leu Glu Glu
115                 120                 125                 130

GGA AGT TAT TCA TTA CCA TCT GAA TTA AGA CGT GTT GAT ATT GCT GTT            587
Gly Ser Tyr Ser Leu Pro Ser Glu Leu Arg Arg Val Asp Ile Ala Val
                135                 140                 145

GTA TCA CGT AAA GAA TGT AAT GAA TTA TAT TCA AAA GCT AAT GCT GAA            635
Val Ser Arg Lys Glu Cys Asn Glu Leu Tyr Ser Lys Ala Asn Ala Glu
            150                 155                 160

GTT ACT GAT AAT ATG ATT TGT GGT GGT GAT GTT GCA AAT GGT GGT AAA            683
```

```
                    Val Thr Asp Asn Met Ile Cys Gly Gly Asp Val Ala Asn Gly Gly Lys
                        165                 170                 175

GAT TCT TGT CAA GGT GAT TCT GGT GGA CCG GTT GTT GAT GTT AAA AAT        731
Asp Ser Cys Gln Gly Asp Ser Gly Gly Pro Val Val Asp Val Lys Asn
180                 185                 190

AAT CAA GTT GTT GGT ATT GTT TCA TGG GGT TAT GGT TGT GCA CGT AAA        779
Asn Gln Val Val Gly Ile Val Ser Trp Gly Tyr Gly Cys Ala Arg Lys
195                 200                 205                 210

GGT TAT CCA GGT GTT TAT ACA CGT GTT GGT AAT TTT ATC GAT TGG ATT        827
Gly Tyr Pro Gly Val Tyr Thr Arg Val Gly Asn Phe Ile Asp Trp Ile
                215                 220                 225

GAA TCA AAA CGT TCA CAG TGATTGATAA AAACAATTTC GACATATAAA               875
Glu Ser Lys Arg Ser Gln
                230

AATTGGCAAA TGATGCCATT ATATGTTATC ATTATGTTTC TGGTGATTCT TTTTCTACTT       935

TTATCATTTT ATTTTATATT CGAGCTGAAA ACAAACAATC ATGATTGTAT AGGGATTTGT       995

TGTTGTTTTT CAATTTAAAA AAATCCAAAA TAAATAAATA AATAATCATT TCAACAAAAA      1055

AAAG                                                                   1059

(2) INFORMATION FOR SEQ ID NO: 2:

(i) SEQUENCE CHARACTERISTICS:
        (A) LENGTH: 261 amino acids
        (B) TYPE: amino acid
        (D) TOPOLOGY: linear (ii) MOLECULE TYPE: protein (xi) SEQUENCE DESCRIPTION: SEQ ID NO: 2:

Met Ile Ile Tyr Asn Ile Leu Ile Val Leu Leu Leu Ala Ile Asn Thr
-29                 -25                 -20                 -15

Leu Ala Asn Pro Ile Leu Pro Ala Ser Pro Asn Ala Thr Ile Val Gly
                -10                 -5                   1

Gly Glu Lys Ala Leu Ala Gly Glu Cys Pro Tyr Gln Ile Ser Leu Gln
     5                  10                  15

Ser Ser Ser His Phe Cys Gly Gly Thr Ile Leu Asp Glu Tyr Trp Ile
20                  25                  30                  35

Leu Thr Ala Ala His Cys Val Ala Gly Gln Thr Ala Ser Lys Leu Ser
                40                  45                  50

Ile Arg Tyr Asn Ser Leu Lys His Ser Leu Gly Gly Glu Lys Ile Ser
                55                  60                  65

Val Ala Lys Ile Phe Ala His Glu Lys Tyr Asp Ser Tyr Gln Ile Asp
            70                  75                  80

Asn Asp Ile Ala Leu Ile Lys Leu Lys Ser Pro Met Lys Leu Asn Gln
85                  90                  95

Lys Asn Ala Lys Ala Val Gly Leu Pro Ala Lys Gly Ser Asp Val Lys
100                 105                 110                 115

Val Gly Asp Gln Val Arg Val Ser Gly Trp Gly Tyr Leu Glu Glu Gly
                120                 125                 130

Ser Tyr Ser Leu Pro Ser Glu Leu Arg Arg Val Asp Ile Ala Val Val
                135                 140                 145

Ser Arg Lys Glu Cys Asn Glu Leu Tyr Ser Lys Ala Asn Ala Glu Val
            150                 155                 160

Thr Asp Asn Met Ile Cys Gly Gly Asp Val Ala Asn Gly Gly Lys Asp
            165                 170                 175

Ser Cys Gln Gly Asp Ser Gly Gly Pro Val Val Asp Val Lys Asn Asn
```

```
                180                 185                 190                 195
Gln Val Val Gly Ile Val Ser Trp Gly Tyr Gly Cys Ala Arg Lys Gly
                    200                 205                 210

Tyr Pro Gly Val Tyr Thr Arg Val Gly Asn Phe Ile Asp Trp Ile Glu
                    215                 220                 225

Ser Lys Arg Ser Gln
            230

(2) INFORMATION FOR SEQ ID NO: 3:

(i) SEQUENCE CHARACTERISTICS:
        (A) LENGTH: 237 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 3:

Ile Val Gly Gly Thr Asp Ala Val Leu Gly Glu Phe Pro Tyr Gln Leu
1               5                   10                  15

Ser Phe Gln Glu Thr Phe Leu Gly Phe Ser Phe His Phe Cys Gly Ala
                20                  25                  30

Ser Ile Tyr Asn Glu Asn Tyr Ala Ile Thr Ala Gly His Cys Val Tyr
            35                  40                  45

Gly Asp Asp Tyr Glu Asn Pro Ser Gly Leu Gln Ile Val Ala Gly Glu
        50                  55                  60

Leu Asp Met Ser Val Asn Glu Gly Ser Glu Gln Thr Ile Thr Val Ser
65                  70                  75                  80

Lys Ile Ile Leu His Glu Asn Phe Asp Tyr Asp Leu Leu Asp Asn Asp
                85                  90                  95

Ile Ser Leu Leu Lys Leu Ser Gly Ser Leu Thr Phe Asn Asn Asn Val
            100                 105                 110

Ala Pro Ile Ala Leu Pro Ala Gln Gly His Thr Ala Thr Gly Asn Val
        115                 120                 125

Ile Val Thr Gly Trp Gly Thr Thr Ser Glu Gly Gly Asn Thr Pro Asp
130                 135                 140

Val Leu Gln Lys Val Thr Val Pro Leu Val Ser Asp Ala Glu Cys Arg
145                 150                 155                 160

Asp Asp Tyr Gly Ala Asp Glu Ile Phe Asp Ser Met Ile Cys Ala Gly
                165                 170                 175

Val Pro Glu Gly Gly Lys Asp Ser Cys Gln Gly Asp Ser Gly Gly Pro
            180                 185                 190

Leu Ala Ala Ser Asp Thr Gly Ser Thr Tyr Leu Ala Gly Ile Val Ser
        195                 200                 205

Trp Gly Tyr Gly Cys Ala Arg Pro Gly Tyr Pro Gly Val Tyr Thr Glu
        210                 215                 220

Val Ser Tyr His Val Asp Trp Ile Lys Ala Asn Ala Val
225                 230                 235

(2) INFORMATION FOR SEQ ID NO: 4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO: 4:

CAGCACTGAC CCTTTTG                                                          17

(2) INFORMATION FOR SEQ ID NO: 5:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 5:

AACAGCTATG ACCATG                                                           16

(2) INFORMATION FOR SEQ ID NO: 6:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 6:

AAAGCTGTTG GATTACCA                                                         18

(2) INFORMATION FOR SEQ ID NO: 7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 7:

TACATCCGAT CCTTTTGC                                                         18

(2) INFORMATION FOR SEQ ID NO: 8:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 8:

TCAGAAAAAG CTTTGGCTGG TGAATCACCA TATCAAAT                                   38

(2) INFORMATION FOR SEQ ID NO: 9:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 9:

```
GAATCAACAC CACCATTAGC AACATCACCA CCGCAAATCA T                41
```

(2) INFORMATION FOR SEQ ID NO: 10:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 10:

```
Met Ile Cys Gly Gly Asp Val Ala Asn Gly Gly Val Asp Ser Glu Gln
1               5                   10                  15
Gly Asp
```

(2) INFORMATION FOR SEQ ID NO: 11:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 11:

```
Met Ile Cys Gly Gly Asp Val Ala Asn Gly Gly Lys Asp Ser Cys Gln
1               5                   10                  15
Asp
```

(2) INFORMATION FOR SEQ ID NO: 12:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 12:

```
Met Thr Leu Asp Gln Thr Asn Ala Lys Pro Val Pro Leu Pro Thr Ser
1               5                   10                  15
```

(2) INFORMATION FOR SEQ ID NO: 13:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 13:

```
Met Lys Leu Asn Gln Lys Asn Ala Lys Ala Val Gly Leu Pro Ala Lys
1               5                   10                  15
```

(2) INFORMATION FOR SEQ ID NO: 14:

(i) SEQUENCE CHARACTERISTICS:
        (A) LENGTH: 7 amino acids

```
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 14:

Asn Asn Gln Val Val Gly Ile
1               5

(2) INFORMATION FOR SEQ ID NO: 15:

(i) SEQUENCE CHARACTERISTICS:
         (A) LENGTH: 31 amino acids
         (B) TYPE: amino acid
         (D) TOPOLOGY: linear (ii) MOLECULE TYPE: peptide (v) FRAGMENT TYPE: N-terminal (xi) SEQUENCE DESCRIPTION: SEQ ID NO: 15:

Ile Val Gly Gly Val Lys Ala Lys Ala Gly Asp Ser Pro Tyr Gln Ile
1               5                   10                  15

Ser Leu Gln Ser Ser Ser His Phe Xaa Gly Gly Ser Ile Leu Asp
            20                  25                  30

(2) INFORMATION FOR SEQ ID NO: 16:

(i) SEQUENCE CHARACTERISTICS:
         (A) LENGTH: 30 amino acids
         (B) TYPE: amino acid
         (D) TOPOLOGY: linear (ii) MOLECULE TYPE: peptide (v) FRAGMENT TYPE: N-terminal (xi) SEQUENCE DESCRIPTION: SEQ ID NO: 16:

Ile Val Gly Gly Glu Lys Ala Leu Ala Gly Gln Ser Pro Tyr Gln Ile
1               5                   10                  15

Ser Leu Gln Ser Ser Ser His Phe Ser Gly Gly Thr Ile Leu
            20                  25                  30

(2) INFORMATION FOR SEQ ID NO: 17:

(i) SEQUENCE CHARACTERISTICS:
         (A) LENGTH: 10 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO: 17:

Met Gly His His His His His His Glu Phe
1               5                   10

(2) INFORMATION FOR SEQ ID NO: 18:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA
```

(xi) SEQUENCE DESCRIPTION: SEQ ID NO: 18:

GCGGATCCAT TGTTGGTGGT                                                                                         20